(12) United States Patent
Jakins et al.

(10) Patent No.: US 10,610,612 B2
(45) Date of Patent: Apr. 7, 2020

(54) SCENT DISPERSION DEVICE

(71) Applicant: MOJILIFE, LLC, Lindon, UT (US)

(72) Inventors: Glenn Jakins, Provo, UT (US); Darrell Jakins, Provo, UT (US); Darin Davis, Lehi, UT (US); Haruyoshi Miyagi, Lehi, UT (US)

( * ) Notice: Subject to any disclaimer, the term of this patent is extended or adjusted under 35 U.S.C. 154(b) by 218 days.

(21) Appl. No.: 15/622,058

(22) Filed: Jun. 13, 2017

(65) Prior Publication Data
US 2017/0360980 A1 Dec. 21, 2017

Related U.S. Application Data

(60) Provisional application No. 62/350,696, filed on Jun. 15, 2016.

(51) Int. Cl.
| | | |
|---|---|---|
| *B01F 3/04* | (2006.01) | |
| *A61L 9/04* | (2006.01) | |
| *A61L 9/12* | (2006.01) | |
| *B05B 9/00* | (2006.01) | |

(52) U.S. Cl.
CPC ............... *A61L 9/04* (2013.01); *A61L 9/122* (2013.01); *A61L 9/127* (2013.01); *B01F 3/04* (2013.01); *B01F 3/04007* (2013.01); *A61L 2209/111* (2013.01); *A61L 2209/12* (2013.01); *A61L 2209/133* (2013.01); *A61L 2209/135* (2013.01); *A61L 2209/14* (2013.01); *B05B 9/00* (2013.01)

(58) Field of Classification Search
CPC ............................... B01F 3/04; B01F 3/04007
USPC ................ 261/30, DIG. 88; 422/124; 96/222
See application file for complete search history.

(56) References Cited

U.S. PATENT DOCUMENTS

| | | | | |
|---|---|---|---|---|
| 3,220,913 | A * | 11/1965 | Thomas | A47G 33/0854 222/187 |
| 5,126,078 | A * | 6/1992 | Steiner | A61L 9/122 261/26 |
| 9,022,365 | B2 * | 5/2015 | Brosmith | B01F 3/04085 261/142 |
| 2010/0284783 | A1 | 11/2010 | Lolmede | |
| 2012/0079945 | A1 | 4/2012 | Roberts | |
| 2014/0145005 | A1 | 5/2014 | Westphal | |
| 2014/0334129 | A1 | 11/2014 | McCavit et al. | |
| 2015/0273099 | A1 | 10/2015 | Habbel | |
| 2016/0089466 | A1 | 3/2016 | McMinn et al. | |
| 2017/0360980 | A1 | 12/2017 | Jakins et al. | |

FOREIGN PATENT DOCUMENTS

| | | |
|---|---|---|
| EP | 2433 656 A1 | 3/2012 |
| WO | 2016205836 A1 | 12/2016 |

* cited by examiner

*Primary Examiner* — Robert A Hopkins
(74) *Attorney, Agent, or Firm* — Amy Fiene PC; James Sonntag

(57) ABSTRACT

A scent delivery system includes a housing that releases a volatile substance from a porous body into the air. The housing may be part of a scent dispersion device that includes volatilization as directed by a fan and a controller within the housing.

20 Claims, 25 Drawing Sheets

SCENT DISPERSION DEVICE

BACKGROUND

Air fresheners are common devices that release scents into the atmosphere. For example, they can be used to help create a comforting home environment or to help maintain the ambience of a professional office space. They can also be used to mask, neutralize, or counteract undesirable odors in hospitals and lavatories. There may even be potential health benefits from scents that boost mood and alleviate stress.

Despite growing use, air fresheners still leave much to be desired. For example, some devices include solid-based ingredients that drip messy wax or leave other residue that requires cleaning after use. Some devices, like wicks and reeds, present problems such as rapid scent loss, poor scent intensity, and lack of character. Some devices require a lengthy time for scent delivery or provide uneven scent distribution. Improvements to scent quality and scent delivery are needed.

Additional improvements are needed for the technology, cost, and design of air fresheners. For example, some devices have an unattractive aesthetic appearance or take up too much space to blend with an environment. Some devices necessitate an electrical outlet which can limit where they are placed in a given room. Some devices are heated which can yield unstable temperatures over time. Some devices have very little means of control once they are opened or turned on, which can shorten the life of the device.

Thus, a need exists for one or more improvements on existing air fresheners.

SUMMARY

An exemplary scent dispersion device includes a housing that releases a volatile substance into the air as directed by a fan. Within the housing, a refill cartridge includes a porous body that retains the volatile substance. Also within the housing is a fan and a controller, the fan being controlled by the controller for directing air up through the housing. The refill cartridge is located in air flow directed by the fan and constructed such that air flow directed from the fan flows through the refill cartridge and out of the housing to volatilize the volatile substance into air.

Also described is a refill cartridge that comprises a cup support containing a porous body that retains the volatile substance. The refill cartridge is located in air flow directed by the fan and constructed such that air flow directed from the fan flows from a bottom of the body to a top of the body along exterior and interior wall surfaces of the body, and out of the housing to volatilize the volatile substance into air.

DETAILED DESCRIPTION

This application claims priority to United States Provisional Patent Application 62/350,696, filed Jun. 15, 2016, which is hereby incorporated by reference.

The following describes one or more improvements to air fresheners in the form of a scent delivery system.

An exemplary scent dispersion device includes a housing that releases a volatile substance into the air as directed by a fan. Within the housing, a refill cartridge includes a porous body that retains the volatile substance. Also within the housing is a fan and a controller, the fan being controlled by the controller for directing air up through the housing. The refill cartridge is located in air flow directed by the fan and constructed such that air flow directed from the fan flows through the refill cartridge and out of the housing to volatilize the volatile substance into air.

Also described is a refill cartridge that comprises a cup support containing a porous body that retains the volatile substance. The refill cartridge is located in air flow directed by the fan and constructed such that air flow directed from the fan flows from a bottom of the body to a top of the body along exterior and interior wall surfaces of the body, and out of the housing to volatilize the volatile substance into air.

Also described is a standalone housing which contains a scent refill cartridge and a fan. The housing is generally cylindrical and vertically aligned to provide an upward air path through the housing and release scent from the cartridge through an orifice of the housing into an external environment. With the device turned on, the fan draws air through air inlets of the housing and forces the air upward through the interior of the housing. The air inlets are below the fan, and can be of any suitable configuration, such as one or more air inlets in the bottom of the housing or on the side of the housing.

The fan is powered by a battery and is controlled by a controller. The battery and controller are contained in the housing at any suitable location, such as below the fan in a position configured to allow air flow.

The battery may be any suitable battery. A rechargeable battery is suitable and may include within the housing recharging circuits. The recharging circuit may include a plug in the housing for a charging jack, or a wireless inductive charging system. While the device is a standalone device, an embodiment includes that an electrical port be used so that the device can be connected to an electrical outlet for activating the device and/or recharging the device.

Figure 1:
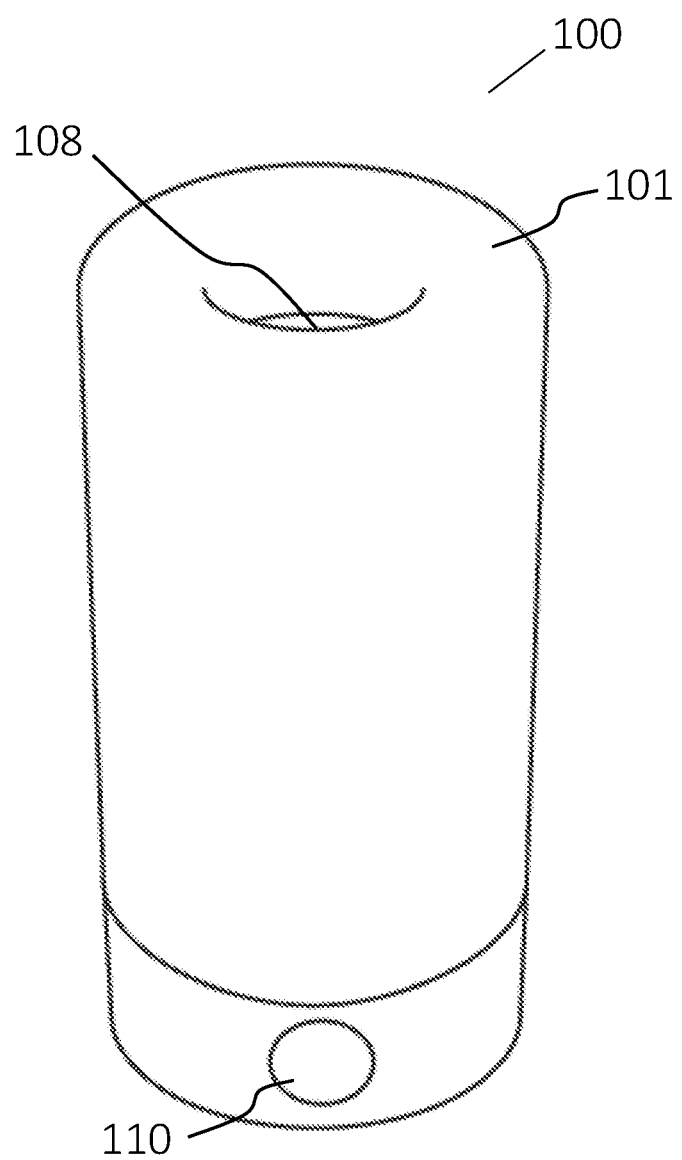
FIG. 1 illustrates a perspective view of a scent dispersion device.

An exemplary device 100 is shown in FIG. 1 and includes housing 101, orifice 108, and a manual input 110. A scented refill cartridge (not shown) is nested within an interior of the housing 101. The manual input 110 may include one or more buttons or other manual mechanism to activate and deactivate the device. The manual input may further provide a means of programming the device. The orifice 108 provides a curved donut hole-like or funnel-shaped opening which promotes scented air flow into the surroundings.

While the device is described having a vertical orientation relative to a ground surface, the device may assume alternate orientations (e.g. horizontal, angled, upside down, etc.) with air flows following the orientations.

Figures 2, 3:
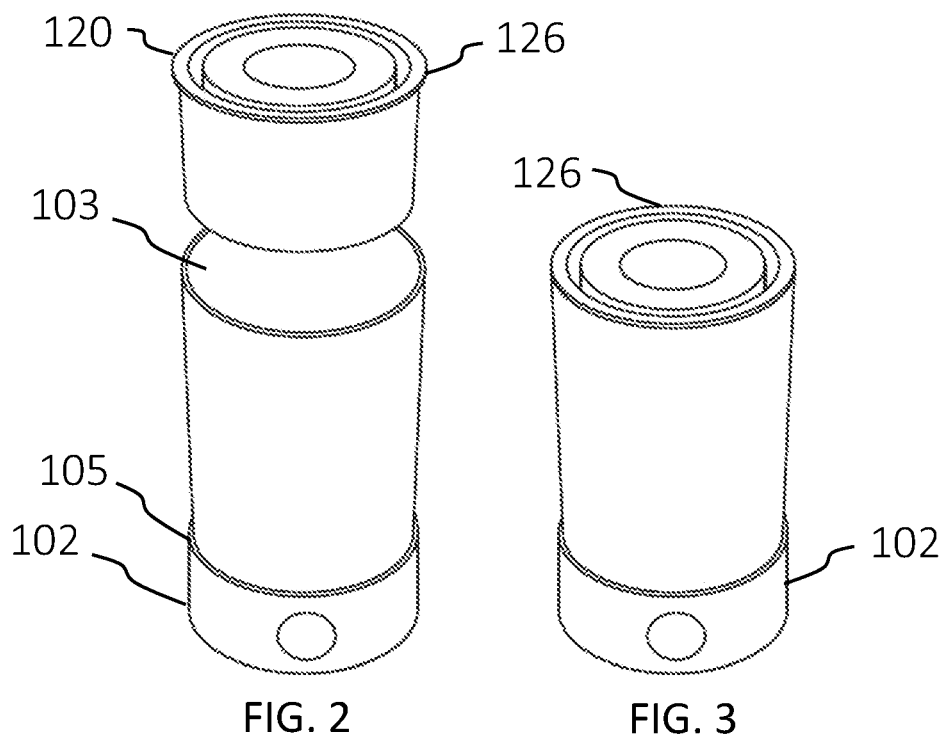
FIG. 2 illustrates a perspective view of a base and a cartridge.
FIG. 3 illustrates a perspective view of a base and a cartridge.
Figures 4, 5:
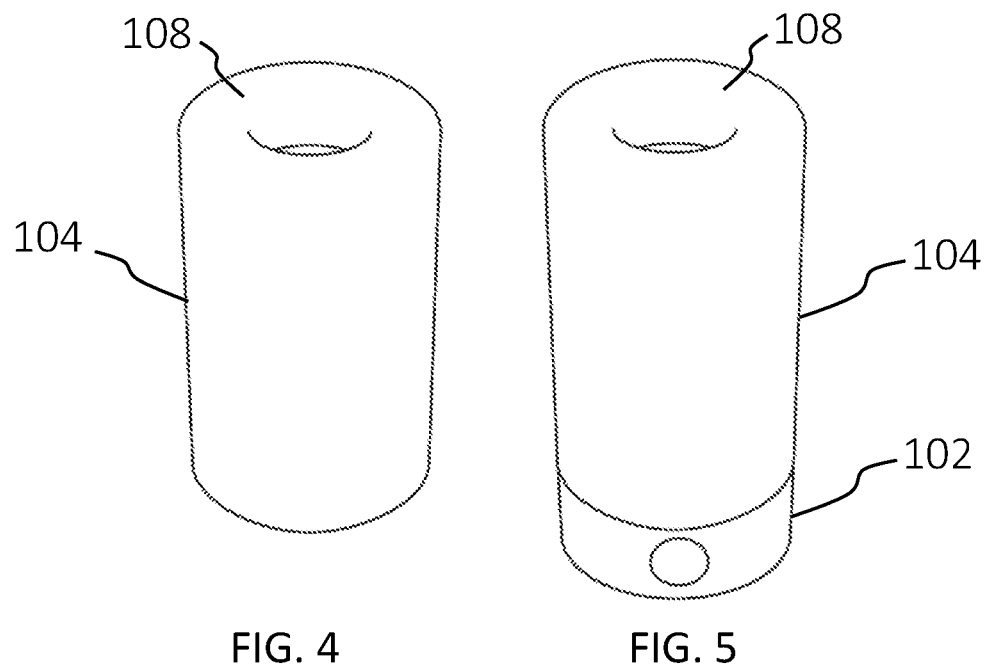
FIG. 4 illustrates a perspective view of a cover.
FIG. 5 illustrates a perspective view of a scent dispersion device.

An embodiment includes that the housing be a single unit. Alternatively, the housing may comprise two parts, a base and a cover. Turning to FIGS. 2, 3, 4, and 5, various views of an exemplary device are shown including a scent refill cartridge 120 and a housing that comprises a base 102 and outer cover 104. To assemble the device, the cartridge 120 is inserted into a cylindrical hollow 103 of the base 102, as seen in FIGS. 2 and 3. The cover 104, as shown in FIGS. 4 and 5, can be engaged and disengaged from the base 102 to allow a user to replace the cartridge 120. The device may be used without the cover 104 and still be fully operable.

Once inside the base 102, the cartridge 120 lays generally flush with the base 102, as shown in FIG. 3. The fit of the cartridge 120 within the base 102 is a snug, friction fit. The cartridge 120 may include an outer lip 126 that extends radially outward from upper edges of the cartridge 120, the outer lip 126 effectively acting as a stop which restricts the cartridge 120 from further longitudinal displacement toward the bottom of the base 102. The outer lip 126 further provides a finger hold for removing the cartridge 120 from the base 102 in order to replace it with a new cartridge.

The outer cover 104 is shown in FIG. 4. A suitable configuration is for the cover 104 to be a hollow cylinder with a dome-like top and that can be slidably engaged to the base 102. The cover 104 further includes an orifice 108 for air to exit through after it is blown up and through the refill cartridge by the fan, the orifice 108 effectively serving as a vent that provides an air path to the outside environment. The orifice 108 may also include components (e.g., scented oils, liquids, etc.) to combine with the scented air exiting the device.

For the base 102, structure may include a shoulder 105 as shown in FIGS. 2 and 3 or other restrictive means that stops the cover 104 from sliding any further on the base 102. Contact between the cover 104 and the shoulder 105 completes attachment of base 102 to cover 104. The cover 104 fits to the outer surface of the base 102 with a sliding or friction fit such that it can be easily attached and removed. The fully attached position of cover 104 and base 102 is shown in FIG. 5.

Figure 6:
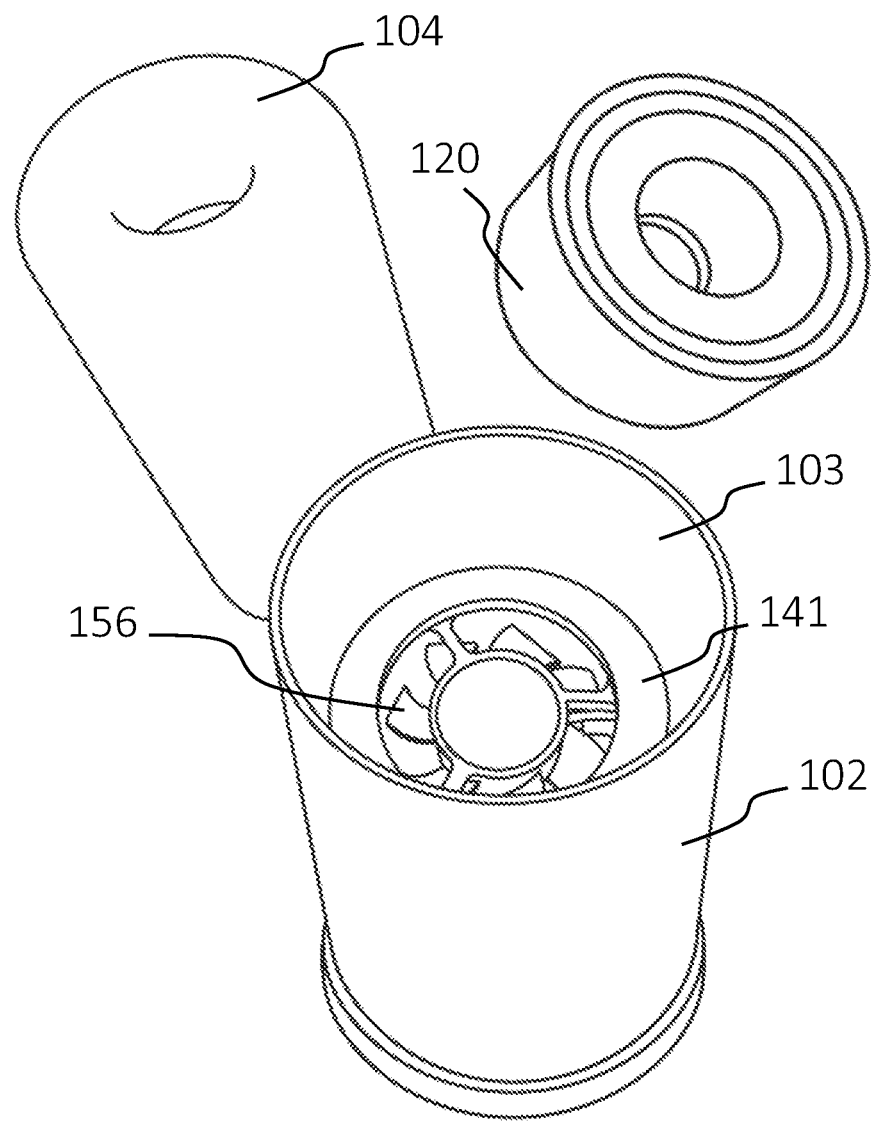
FIG. 6 illustrates a perspective view of an unassembled scent dispersion device including a base, cover, and cartridge.

Turning to FIG. 6, the cover 104, cartridge 120, and base 102 are shown. A fan 156 is located within the hollow 103 of the base 102 and is configured to push air upward toward the top of the base 102. The fan includes air holes such as the holes shown which allow air to travel in a generally unobstructed path through the fan. Located above the fan 156 is an annular flange 141 or shoulder that extends radially inward from the interior walls of the hollow 103. The width of the flange 141 provides a support for the cartridge 120. The cartridge 120 and flange 141 can be stacked so as to provide a generally unobstructed air flow through the cartridge 120.

When the cartridge 120 is inserted into the hollow 103 and a cover 104 is placed over the base 102, there is an interior space defined between the top of the cover 104 and the top of the cartridge 120 in which air flows toward the orifice 108. The air flow in the interior space can be improved by shaping or streamlining the interior space. For example, air flow may be directed outside of the orifice 108 by contours, such as angled and/or curved surfaces along the underside of the top of the cover 104. This can be accomplished by molding a shaped interior during molding of the cover 104.

Figure 7:
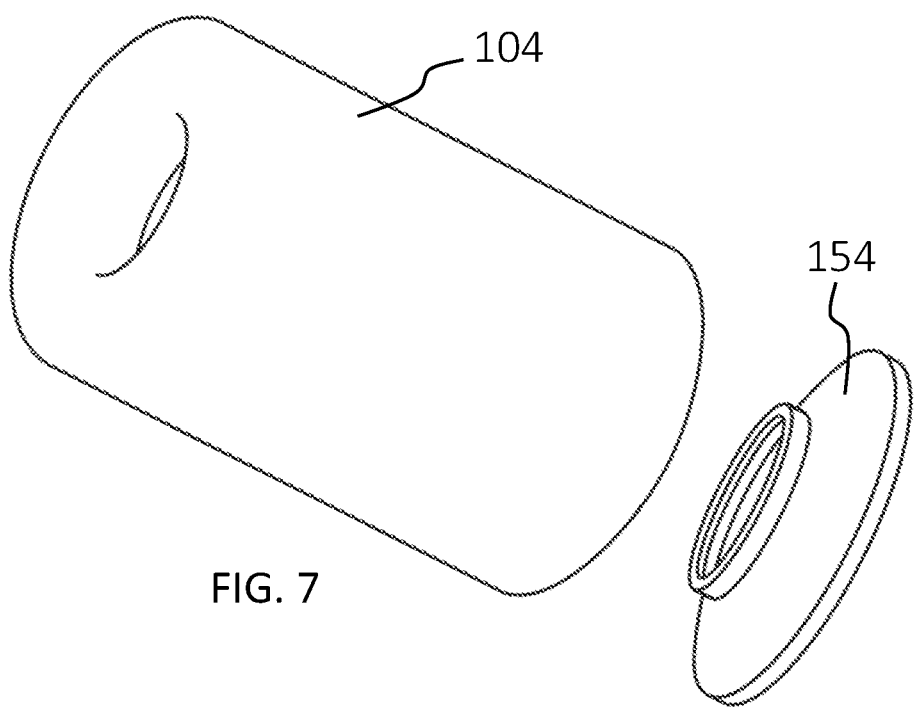
FIG. 7 illustrates a perspective view of a cover and an insert ring.
Figure 8:
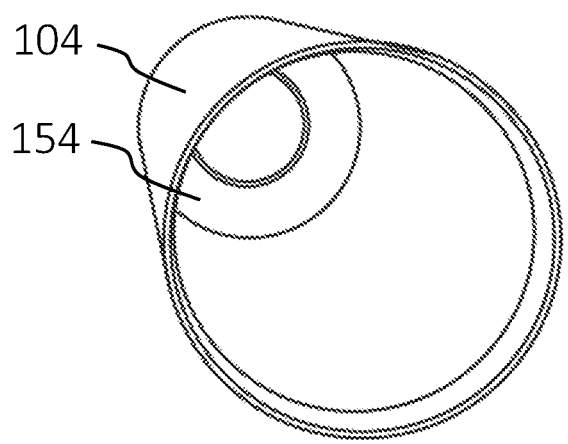
FIG. 8 illustrates a perspective view of a cover and an insert ring.
Figure 9:
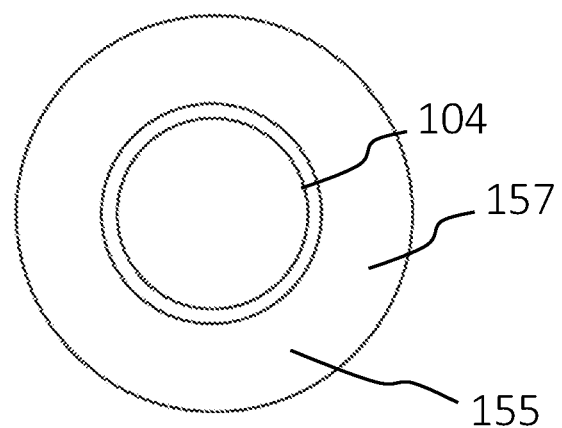
FIG. 9 illustrates a top view of an insert ring.
Figure 10:
FIG. 10 illustrates a perspective view of an insert ring.
Figure 11:
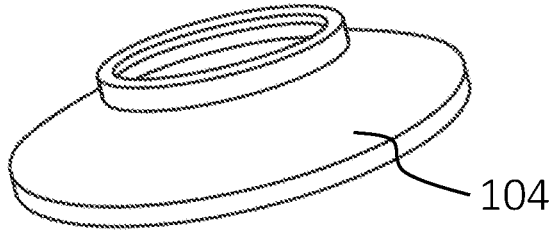
FIG. 11 illustrates a perspective view of an insert ring.
Figure 12:
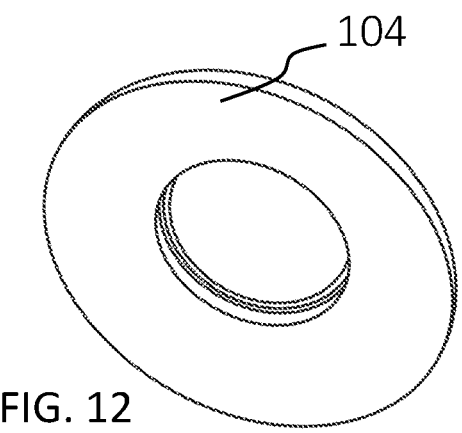
FIG. 12 illustrates a perspective view of an insert ring.
Figure 24:
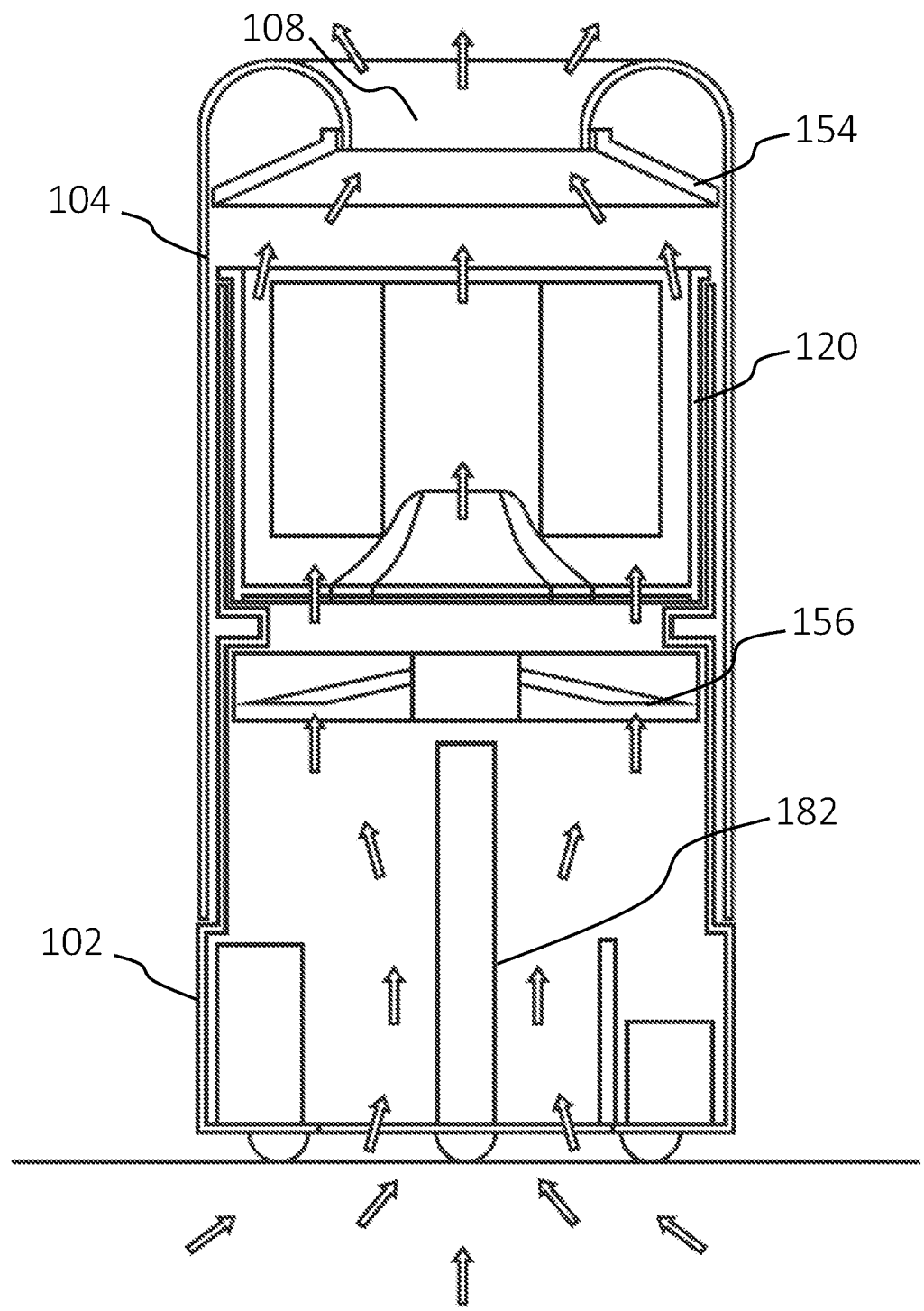
FIG. 24 illustrates exemplary air flows through a scent dispersion device.
Figure 25:
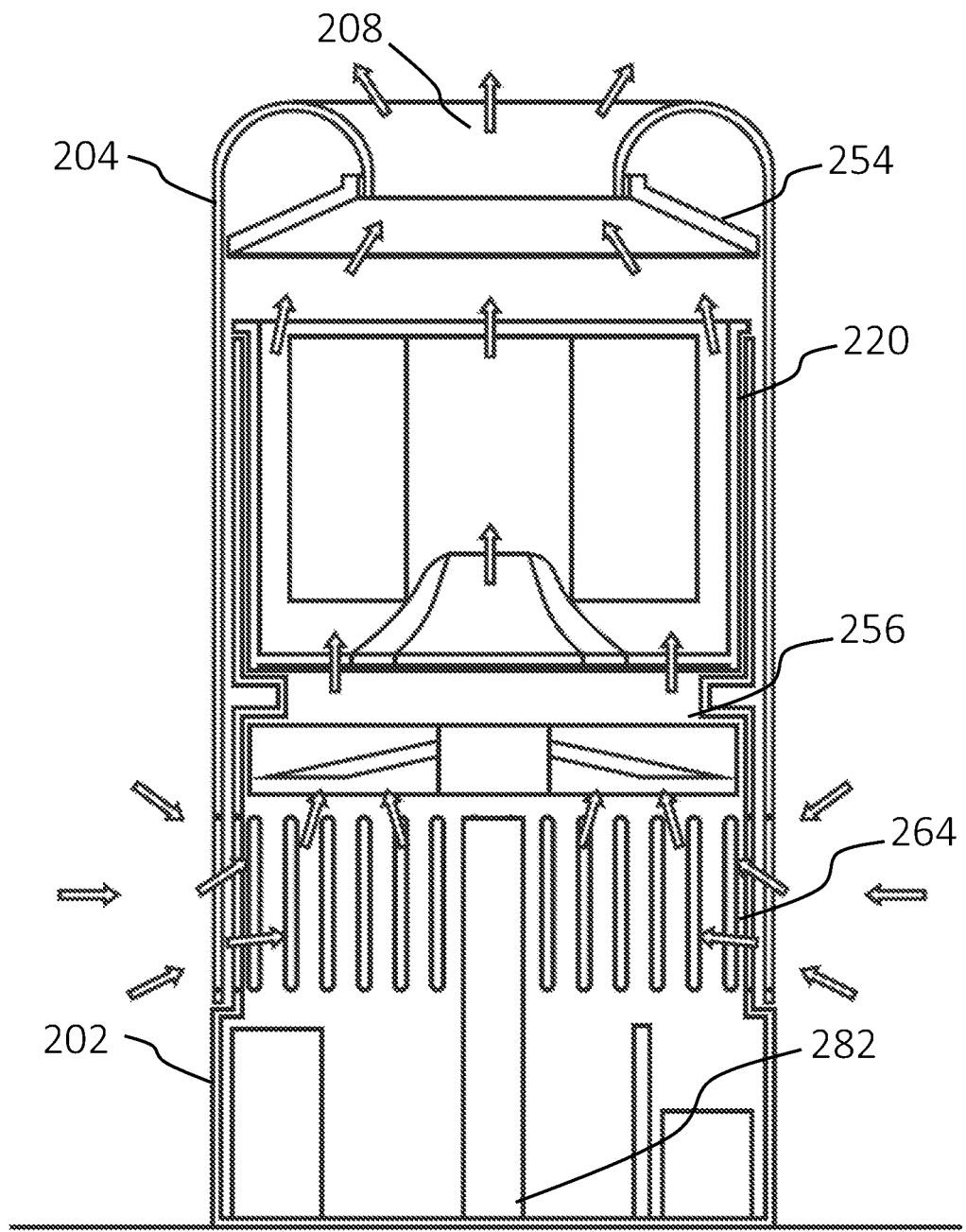
FIG. 25 illustrates exemplary air flows through a scent dispersion device.

Alternatively, as shown in FIG. 7, a removable insert ring 154 may be provided as an insert for the cover 104. The insert ring 154 may be described as a flexible disc with angled sides and an axial hole therethrough. The insert ring 154 is inserted into the hollow interior of the cover 104 and pressed up against the underside of the cover 104. In an attached position, the insert ring 154 is held in place underneath the top of the cover 104 by a friction fit or other attachment (e.g., bonded, screwed together, etc.). The hole of the ring is concentric with the orifice 108 of the cover 104, the hole of the ring being similar in diameter. For example, the hole of the ring may be smaller in diameter to fit at least partially within the orifice, be of the same diameter as the orifice, or be slightly larger in diameter than the orifice 108 to fit around inner walls of the orifice. An exemplary attached position of the insert ring and cover is illustrated in FIGS. 8, 24, and 25.

Various views of the insert ring are provided in FIGS. 9, 10, 11, and 12. The ring is defined by a ring wall 155 that can be inserted at least partially around or within the orifice 108 of the cover 104. The ring includes a wing 157 that extends radially outward and slightly angles away from the ring wall 155. The top surface of the ring wall 155 is generally flat, or may be rounded in a concave or convex manner. The bottom surface of the wing 104 is also generally flat or rounded in a slightly concave or convex manner. With the insert ring 104 in place, air pockets getting trapped within the top rounded dome of the cover 104 are prevented because the wing 104 covers the rounded concave or donut shape surface of the underside of the cover 104, and is configured to direct air flow smoothly out of the housing.

Figure 13:
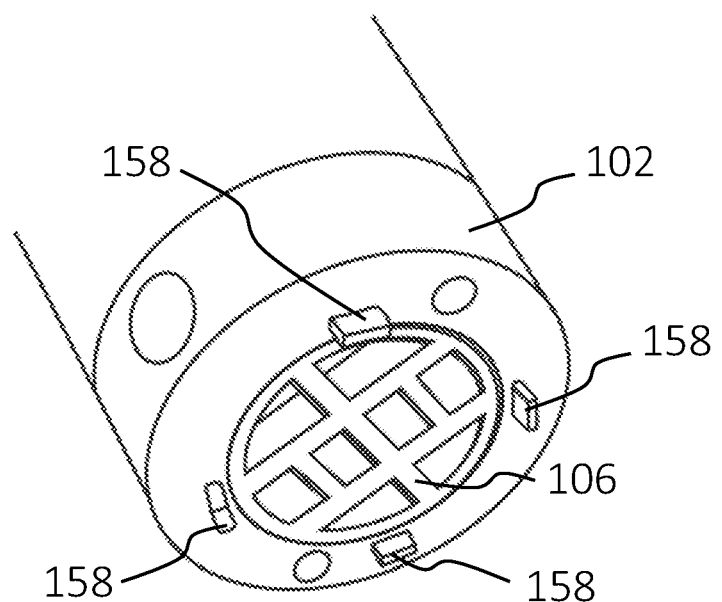
FIG. 13 illustrates a perspective view of a bottom portion of a base.
Figure 14:
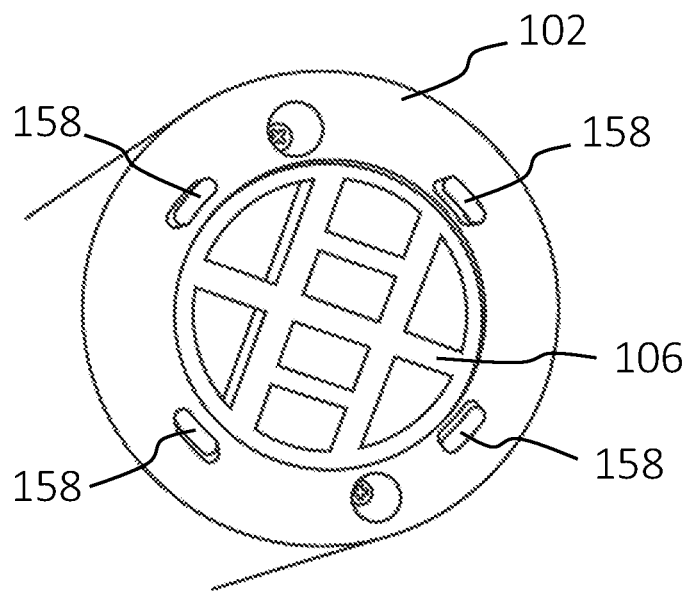
FIG. 14 illustrates a perspective view of a bottom portion of a base.

The air flow through the housing originates from one or more air inlets located on side walls of the housing 101 or underneath the base 102. Passage of air flow from underneath the housing 101 is enabled by raising the base 102 above a ground surface level. An exemplary plurality of legs 158 are shown underneath the base 102 in FIGS. 13 and 14. Each leg 158 extends downward from underneath the base 102. The legs 158 are spaced apart so as to support the base and allow for air flow. As shown, the legs 158 are spaced on opposite sides from each other on the underside of the base 102 and are sufficiently narrow in width to allow air flow circulation underneath the base 102. The plurality of legs may raise the housing by a height. Non-limiting exemplary heights include 0.10-0.20 cm, 0.21-0.25 cm, 0.26-0.30 cm, 0.31-0.40, 0.41-0.50 cm, etc.

In addition, the underneath surface of the base 102 may include a panel 106 that defines one or more air inlets. An air inlet may be any one or more of an opening, vent, flue, shaft, duct, channel, passage, pipe, or pipeline. The panel 106 may be molded as part of the base 102, or alternatively, the panel 106 may be a separate unit that attaches to the base 102. The panel 106 may be centrally located on the underneath surface of the base 102 as shown. The panel 106 is configured such that air may be directed up from underneath the base 102 and through the housing in a generally vertical direction.

The base and cover of the scent dispersion device are configured to allow easy removal and replacement of the scented refill cartridge. The cartridge is likewise configured to be easily removable and replaceable from the base. The cartridge provides structure to direct an air stream directed against the cartridge and disperse a scent into the surrounding environment. A suitable configuration includes a solid porous material in a cylindrical form.

Figure 15:
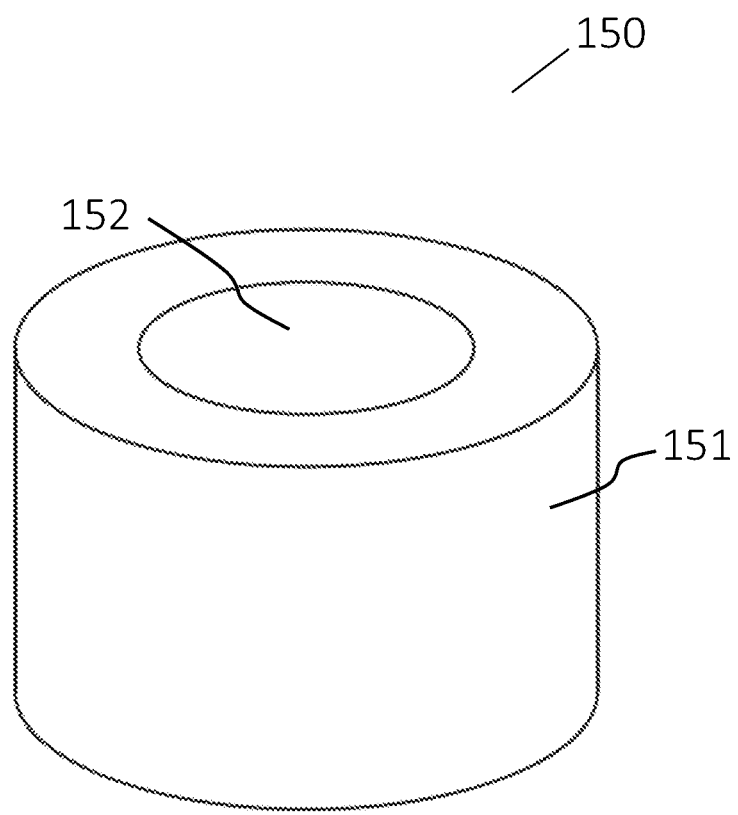
FIG. 15 illustrates a perspective view of a wick.

Turning to FIG. 15, a porous material in the form of an exemplary wick 150 is shown. Being porous allows the wick 150 to hold a volatile liquid scent. Suitable porous materials for the wick 150 include, for example, one or more of dried wood pulp, other wood forms, cellulose, foams of natural or synthetic polymers, natural or synthetic fibers, ceramics, porcelain, plastics, fabrics, cotton, glass, and composites thereof.

The wick may take a variety of shapes, such as a sphere, ovoid, ellipsoid, pyramid, trapezoid, polyhedron, cuboid, etc. The wick 150 as shown includes a generally cylindrical body 151 formed with a hole 152 or central axial opening therethrough. The cylindrical body 151 includes a generally flat top surface and a generally flat bottom surface. The body 151 further includes generally flat exterior surface walls and generally flat interior surface walls.

The volatile liquid scent can be any suitable diluted or undiluted oil or water-based scent material in the liquid state that volatilizes into vapor in air. This includes scented oils, essential oils, and any suitable fragrance composition. Applications may further include odoriferous and stinky materials. Also contemplated are volatile materials that have a medicinal, biological, or like application. The device does not include a heater to volatilize the liquid, so suitable materials are those that vaporize or evaporate sufficiently in the fan directed air stream without heating.

Figure 16:
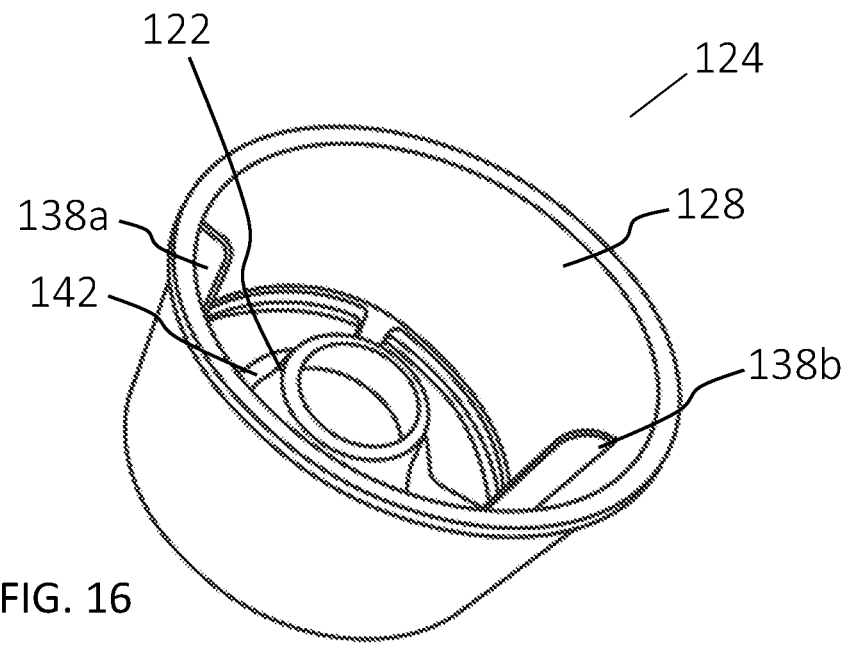
FIG. 16 illustrates a perspective view of a cup support.
Figure 17:
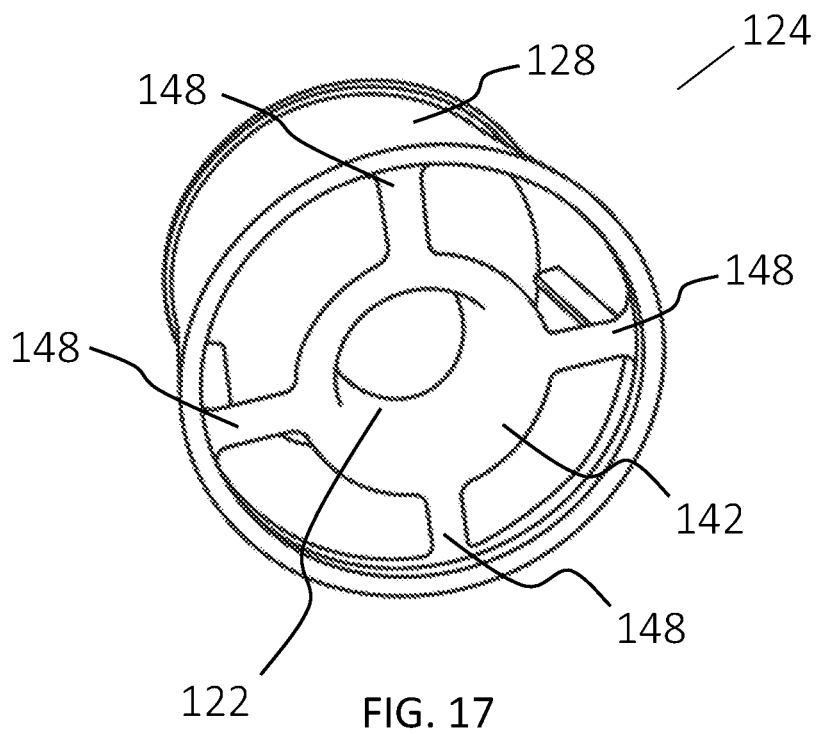
FIG. 17 illustrates a perspective view of a cup support.

As shown in FIGS. 16 and 17, an exemplary suitable cup support 124 for the wick 150 is shown. To increase the surface area for air flow and emission of scent from the porous material, the cup support 124 includes one or more holes on both ends. The cup support 124 as shown includes structure to direct air into the holes and thus diffuse evaporated scent into the air stream.

The cup support 124 includes solid lateral side walls 128, a cup hole 122 or central axial opening, and a bottom forming a cup-like shape. The walls 128 may be vapor impermeable. The walls 128 and bottom define a space for containing a wick. The bottom includes one or more of a narrowing stream constrictor 142 and a support section 148. As shown in FIGS. 16 and 17, the narrowing stream constrictor 142 is surrounded annularly by the support section 148.

The narrowing constrictor 142 of the cup support 124 includes walls that form a funnel shape. In the vertical direction of the cup hole 122, the curved walls start by defining a large central opening at the bottom of the cup and then gradually curve and taper inward to direct and streamline the air flow upward toward the top of the cup. The walls are configured to extend at least partially within the cup space. Upper edges of the walls form a smaller opening relative to the large central opening.

In the downward facing direction, the curved walls that define the large opening at the bottom of the cup curve downward and radially outward to a horizontally extending direction so as to be partially extended toward the side walls of the cup, perpendicular to the cup axis. In this manner, the walls radially extend outward to form an annular ridge around the large opening, and may be used to support the wick in certain embodiments.

Extending radially outward from the narrowing constrictor 142 is a support section. The support section 148 includes one or more holes that provide space for air to flow upward into the cartridge from the fan. An exemplary support section 148 is shown formed by four arms that extend radially outward in opposing directions from the constrictor 142 and connect with side walls 128 of the cup support 124.

Alternatives include a bottom structure without a narrowing constrictor and/or without a support section. The bottom structure may simply have holes and/or alternative structure that allows air to flow and/or streamlines air flow through the cartridge. Also, the wick itself may have curvature that streamlines air flow. For example, inner walls may curve outwardly similar in nature to the curvature of the constrictor.

The cup support 124 may include vertical ridges 138a and 138b that are configured to hold the wick in place relative to the cup support 124. As shown in FIGS. 16 and 17, the vertical ridges 138a and 138b extend radially inward and vertically upward from the base support.

The ridges are diametrically opposed along interior walls of the cup support 124 so as to engage the wick from opposite sides. Distal ends of the ridges 138a and 138b converge with two of the four diametrically opposed arms as shown. The ridges and arms have planar alignment, which helps to streamline air flow. Variations may include other configurations, for example, four ridges with each of the ridges in alignment with respective arms.

At proximal ends, the ridges 138a and 138b have curved upper edges rather than sharp edges that could dig in and tear or otherwise damage the wick 150. The curved upper edges further allow the wick 150 to easily slide in and out of the cup support 124. At distal ends, alternatives include that the ridges curve or bend to form horizontal supports for the wick and that prevent the wick from longitudinal displacement toward the distal end of the cup.

Figure 18:
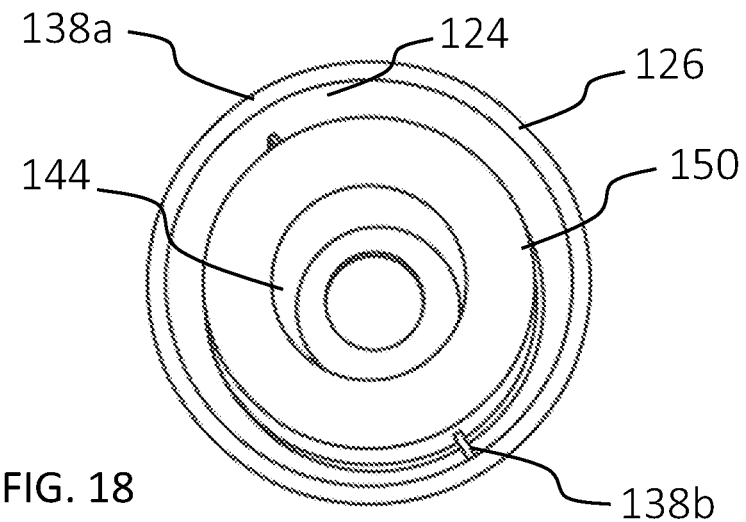
FIG. 18 illustrates a perspective view of a refill cartridge.
Figure 19:
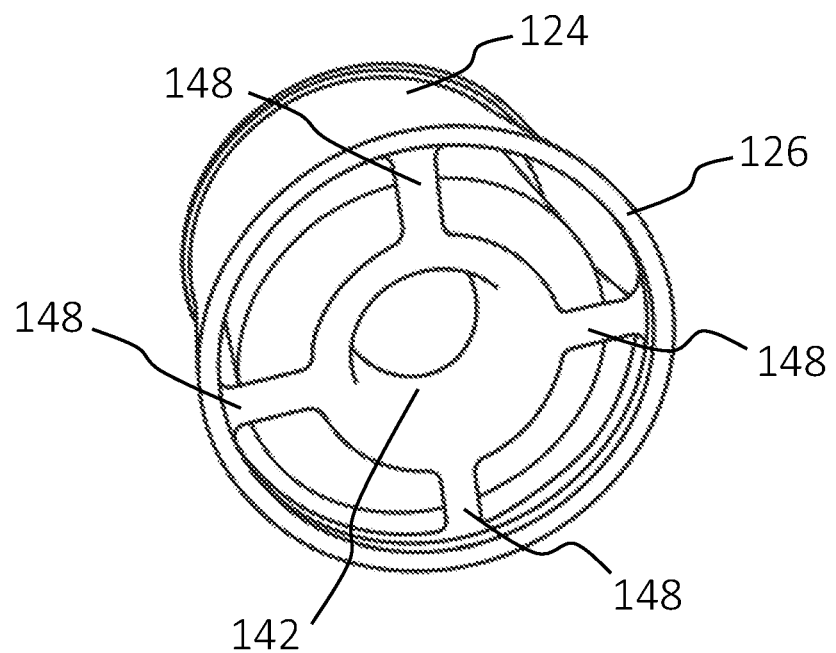
FIG. 19 illustrates a perspective view of a refill cartridge.

In FIGS. 18 and 19, the wick 150 is shown positioned within the interior space defined by the cup support 124. The wick 150 may be held in place by the ridges 138a and 138b and/or be partially supported by the support section 148 and/or the constrictor 142. The wick 150 is centered coaxially within the cup support 124, the hole of the wick 150 being generally aligned with a central hole of the cup support 124. The constrictor 142 at least partially extends up through the opening of the wick 150. The central hole of the wick 150 is generally in axially alignment with the funnel opening of the constrictor 142.

Also, the outer diameter of the wick 150 is less than the inner diameter of the cup support 124 so as to leave a vertical annular space around the outer walls of the wick 150. The space defined between inner walls of the cup support and outer walls of the wick provide for air pathways along the exterior wall surface of the wick 150. The annular space provides air pathways that go from the bottom opening of the cup support 124 to the top opening of the cup support 124. Air flows can travel along sidewalls of the wick 150 and within the interior walls of the wick. The contact between the exterior surface walls of the cup support 124 and inner walls of the base 102 is a friction fit, negating any space therein for air to flow.

Initially, air flows up from the base openings and then bifurcates to the constrictor 142 and the annular space around exterior surface walls of the wick. The constrictor 142 directs air flow along inner walls of the wick 150 while the space between the cup and the wick directs air flow along outer walls of the wick 150. With openings provided by the support section 148 at the bottom of the wick, air that flows to the exterior surface walls also flows along the bottom surface of the wick 150. The two air flows (i.e., flow along exterior surface walls of the wick and flow along inner walls of the wick) converge at the top of the wick 150, to flow along the top surface of the wick 150 and up toward the top of the housing and out through the orifice of the cover.

With the inner hole of the wick, outer walls of the wick, and top and bottom surfaces of the wick exposed to air flow, the wick is configured for an even air flow distribution over the entire outer surface, or a substantial portion of the outer surface, of the wick, which results in efficient evaporation and optimal scent release through the top of the housing.

The cup support 124 contains a scented wick 150 that has absorbed or otherwise retained a liquid fragrance or other volatile liquid. The cup support is advantageous for several reasons. For example, the cup support keeps fingers clean during handling, including set up, clean up, replacement, use, etc. This is unlike other aroma devices that use wax that drips onto the ground and that must be cleaned off or otherwise removed from the device. The wick is also advantageous because it is long-lasting, with steady scent released into the air as provided by a fan. The distribution of the scent is favorable because of the air pathways that direct air flow steadily and efficiently. There is no need to wait for a device to heat up or have other delays in release of scent because the fan and wick combination provide an instant scent release that permeates the atmosphere. Other advantages are readily apparent.

Figure 20:
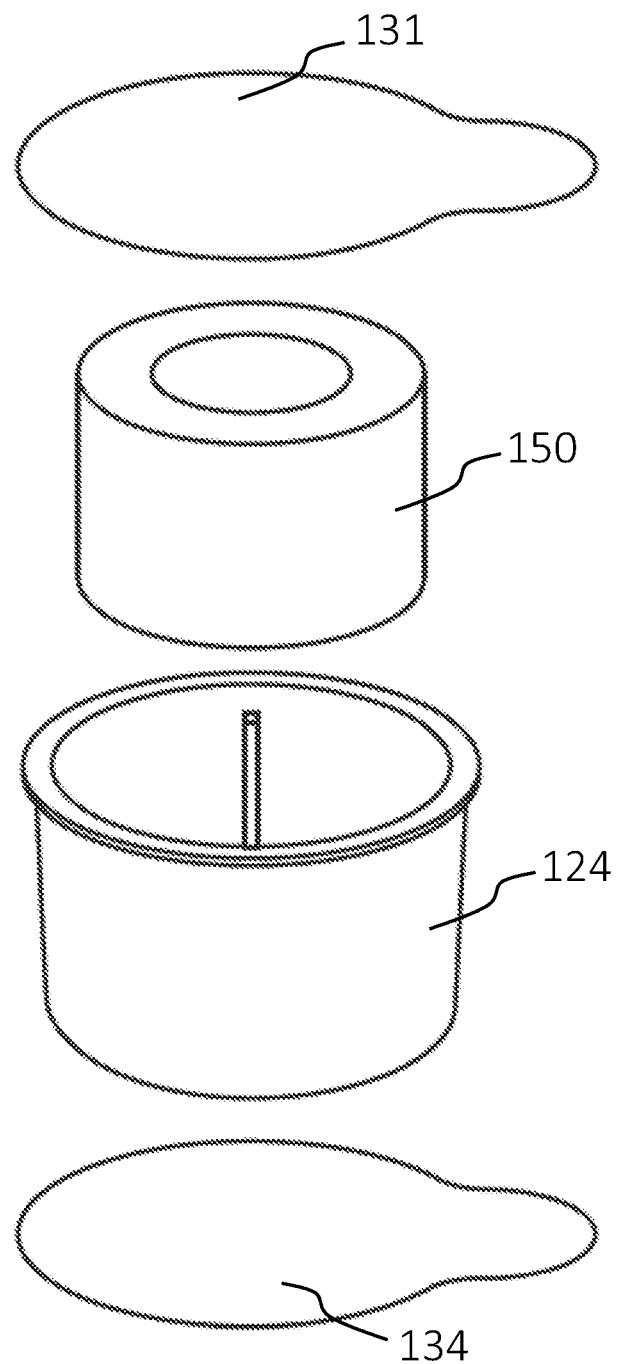
FIG. 20 illustrates an extruded view of a refill cartridge with top and bottom seals.

When the life of a refill cartridge in the device is spent, it can be replaced with a new one from storage. To prevent the liquid fragrance, or other volatile liquid, from being lost during storage, the stored refill cartridge is suitably sealed in packaging or a container. Turning to FIG. 20, components of a cartridge are shown in an extruded view including a wick 150, a support cup 124, a top seal 131, and a bottom seal 134. The top and bottom seals 131 and 134 cover respective top and bottom openings of the refill cartridge during storage. The seals are comprised of a flexible impermeable material (e.g., metal foil or polymer film) that are joined to the support cup with a removable adhesive to seal the interior off from scent release.

The seals lay generally flat on top and bottom surfaces of the refill cartridge. The height of the wick 150 is less than the height of the cup support 124 so that the top seal 131 lays flat across the top opening of the cup support. Also, the constrictor and support section are configured to be fully contained within the cup support so that the bottom seal 134 lays flat across the bottom opening of the cup support.

Non-limiting exemplary dimensions of the wick include an outer diameter between 1.25 to 1.59 inches, 1.60 to 1.75 inches, and 1.76 to 2.00 inches, an inner diameter between 0.50 to 1.00 inch, 1.10 to 1.25 inches, and 1.26 to 1.50 inches, and a height between 0.75 to 1.00 inch, 1.10 inch to 1.25 inches, and 1.26 inches to 2.00 inches. Other dimensions are anticipated.

Figure 21:
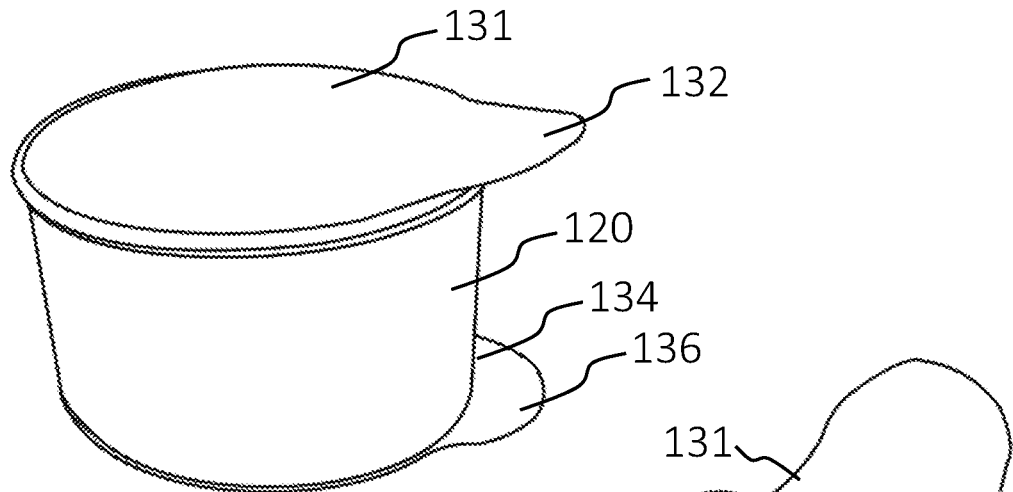
FIG. 21 illustrates a perspective view of a refill cartridge with top and bottom seals.
Figure 22:
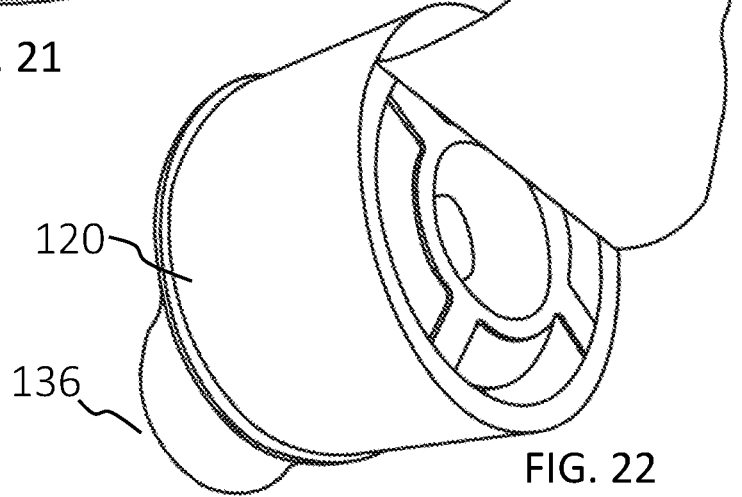
FIG. 22 illustrates a perspective view of a refill cartridge with top and bottom seals.
Figure 23:
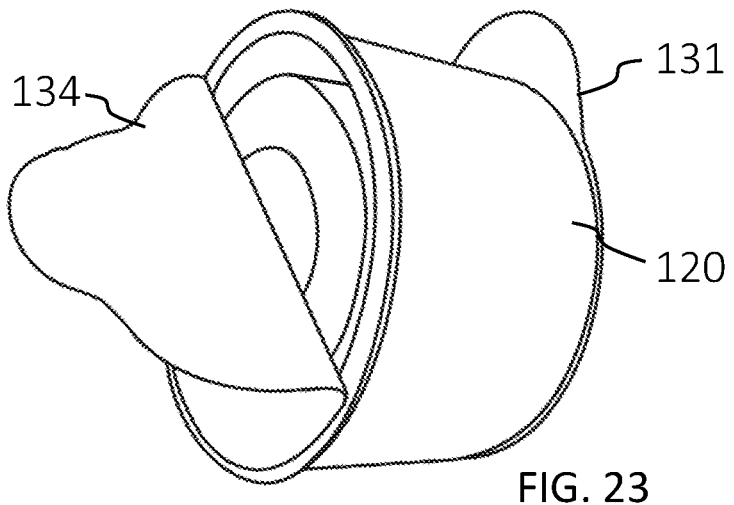
FIG. 23 illustrates a perspective view of a refill cartridge with top and bottom seals.

FIGS. 21, 22, and 23 show an exemplary cartridge 120 with a top seal 131 and a bottom seal 134 and respective pull tabs 132 and 136 for opening the cartridge 120. The top and bottom seals 131 and 134 extend to circumferential edges of the top and bottom openings of the cup support. Pull tabs 132 and 136 are extended members of the seals that extend radially outward from the circumferential edges so that the user may easily grasp them to remove top and bottom seals 131 and 134 by peeling or pulling them away from the cartridge 120. Top and bottom seals 131 and 134 are removed prior to the cartridge 120 being inserted into the base 102. An embodiment includes that the seals be re-sealable so as to further the life of the wick 150 after each use.

To use the device, the seals are removed from the refill cartridge 120 and the refill cartridge 120 is inserted into the base 102. The cover 104 with insert ring 154 is placed over the base 102 to form the housing. Once activated, the fan 156 directs air through bottom air inlets underneath the base 102 and through the housing as pushed by the fan until it reaches the top orifice and exits the housing. Air flows are shown in FIG. 24.

The fan 156 is shown located generally near or slightly below the midline of the base. A suitable location of the refill cartridge 120 is directly above the fan 156 or as close as practical to the fan 156. In an alternative configuration, the cartridge is placed below the fan or in a different position that still utilizes air flow to push air and thereby release scent from the cartridge.

In the example shown, a controller 182 is positioned vertically lengthwise rather than horizontally lengthwise to optimize passage of air flow up and around the controller 182. The controller 182 controls the fan 156. In addition to turning the fan 156 on or off, the controller 182 also controls the fan speed. The controller 182 may include settings so that the device turns on at intervals of time, for example, every 30 minutes, every 60 minutes, or every 90 minutes. The controller 182 may also provide the user with any suitable system including wireless communication, such as Wi-Fi or Bluetooth. This can be in conjunction with an app on a cell phone or tablet, or with a dedicated user interface. With wireless communication, the controller may be in communication with any suitable device to provide data or user input. For example, sensors (motion, chemical, particle, temperature, moisture, etc.) may be provided to signal an event or condition. The controller may be programmable to determine operation of the fan based upon sensor and user inputs, and the time.

The controller is programmable and can incorporate almost any suitable function for operating the fan and any optional light and other added components (e.g. LED, sound generator, sensor, etc.). With wireless communication combined with a user interface and any number of various devices, the fan can be regulated based upon time, environmental conditions, preset settings, and communications from the user. This allows the operation of the device to be efficient and power saving.

Accordingly, the battery can last a long time due to low power consumption by efficient control of the fan operation by the controller. In addition, the air flow path is designed for efficiency lowering power consumption. Furthermore, the present device does not require a heater, which is power hungry and inefficient for dispersing materials into the air.

The device can operate for a long time without intervention or maintenance due to the long battery life, and the potentially large capacity of the refill cartridge, which is only limited by dimensions of the device. The device is standalone since it is battery powered, and wirelessly controlled and regulated.

The components of the device may be constructed by any suitable method, such as any one of or a combination of molding, milling, machining, bending, stamping, cutting or the like. The components may be manufactured of any suitable material which includes any one or a combination or composite of thermosetting or thermoplastic polymers that are synthetic or natural (polyethylene, polypropylene, nylon, etc.), metals (aluminum, steel, etc.), and/or wood.

The vaporization of the scent is assisted by the air flow, and not by a heater. Air flow is optimized by providing a straight upward vertical air flow up through and out of the device, with streamlining and construction to minimize friction and impediments to the air flow. Instead of increasing air flow with a larger fan, air flow is optimized by this streamlining, allowing a relatively low power consumption of the fan while maintaining a large air flow.

In tests of an exemplary prototype an air flow as high as 2.2 meters per second measured by anemometer near the exit was obtained. Due to the inner wall design directing air flow out the top opening, the device almost works like a blow gun. Despite a relatively small size of the device, the fragrance/room coverage is quite significant. It is expected that a higher air flow and air speed can be obtained by optimizing the design and increasing the size of the device. The device can clearly be scaled up and down depending on where it is to be used and how it is to be used.

The device is easily maintained. Assembly and disassembly for maintenance, refill cartridge replacement, change of outer cover, can be accomplished by sliding components and locking components without the use of tools or other like assists.

Turning to FIG. 25, an alternative device is shown that includes side air inlets 264. The side air inlets go through a visible portion of the base that is not concealed by the cover or alternatively, through the base and cover, with respective air inlets in alignment. With side air inlets, air is pulled through the housing from the side air inlets rather than through the bottom of the base 202. The rest of the air flow is similar, being directed through the cartridge 220 to the orifice 208 of the cover 204. The insert ring may also be used 254 like it was before. The device need not be raised from the ground surface to draw air flow. An embodiment may include both side air inlets and bottom air inlets, in which case the device would still be raised from the ground surface. The controller 282 may be placed vertically as shown, however, it may instead be placed in other orientations. For example, a horizontal orientation that is below the side openings may be used to avoid obstruction of air flow.

Note that the air inlets, whether they be inlets underneath the base or side inlets, may be adjusted. For example, the inlets may include vents that allow the user to vary the opening size of the inlets and thus modify the rate of air flow. Other means of controlling air flow may be used as well.

Figure 26:
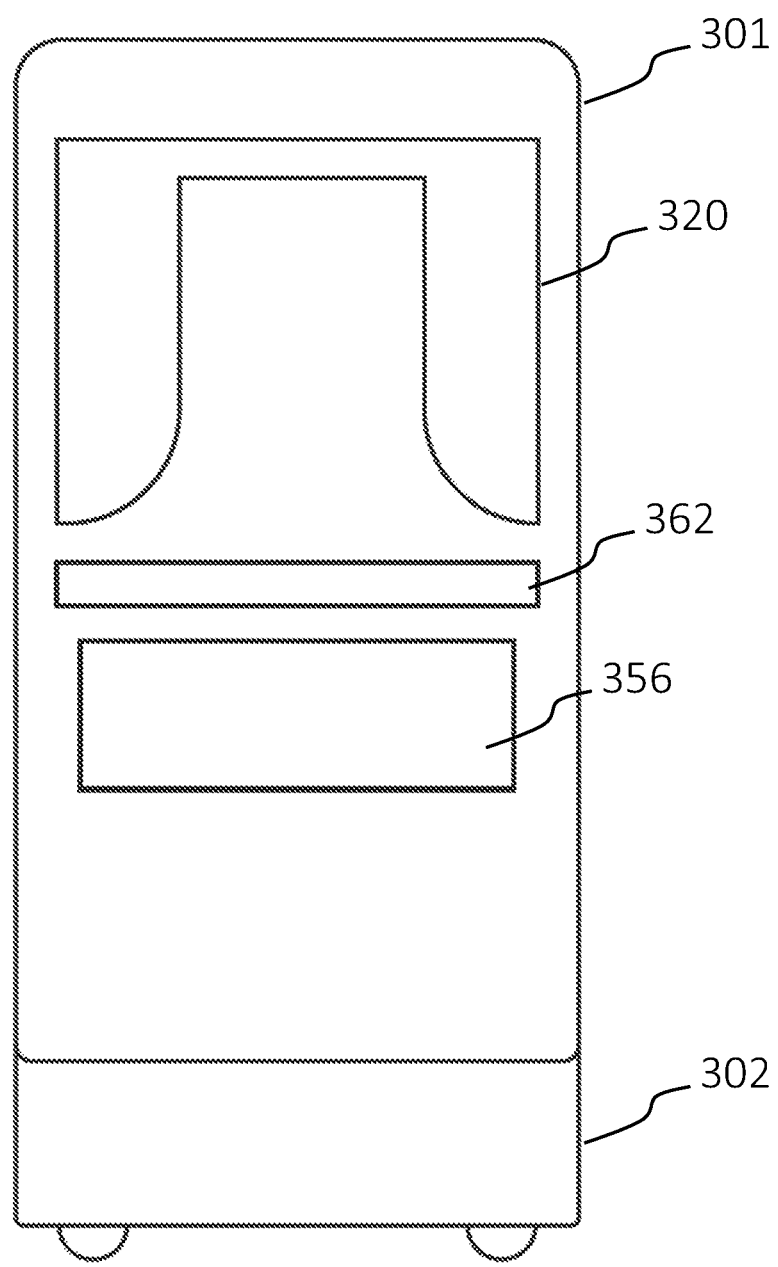
FIG. 26 illustrates a scent dispersion device with a filter.

A filter may be placed in an appropriate place to scrub the air. The directed air by the fan flows through the filter before or after it flows through the fan within the housing. In FIG. 26, an embodiment of the device is shown that includes a filter 362 positioned between the fan 356 and the refill cartridge 320. The filter 362 is configured to scrub the air before the air flows through the refill cartridge and out of the top of the housing 301. In this manner, the quality of air can be improved and allow inhalation and enjoyment of the scented air to be improved. The filter 362 is placed in the device in the same manner as the cartridge by simply inserting the filter 362 through the top opening of the base 302.

The filter 362 may have a friction fit against the sides of the interior walls of the base 302 to hold it in place. Also, an inner shoulder or radial flange within the base 302 may be used to support the filter 362, similar to the shoulder or flange that supports the cartridge 320. Alternatively, the filter 362 may rest against a protective covering of the fan 362. The filter 104 may be a replaceable, removable component.

Variations on the filter include the use of ionization, air cleaners, and/or air purification systems. The structure may include that the filter be positioned just above the fan, and then the other cleaning means, such as the ionization, air cleaner, and/or air purification system, be positioned just above the filter. The directed air by the fan may flow through the filter before or after it flows through the other cleaning means within the housing. Alternatively, other stacking arrangements may be used. Also, one or more of the filter, ionization, air cleaners, and/or air purification systems may be combined as one or more units.

One or more of the other components may be replaceable and reusable like the filter. In some instances, one or more of the components may be used instead of the filter, in which case, they would by positioned just above the fan, below the fan, or in another suitable arrangement that is configured to provide air flow through the housing in a manner that still releases scent.

Figure 27:
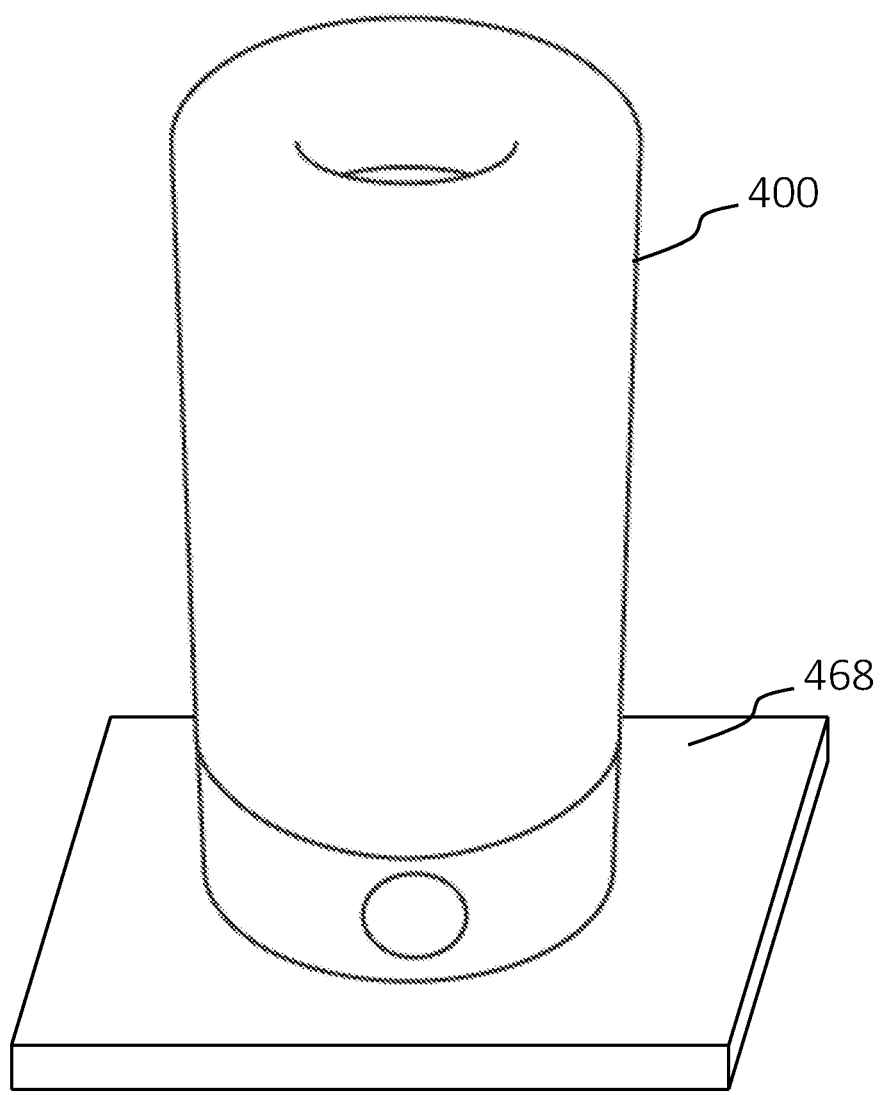
FIG. 27 illustrates a scent dispersion device including a docking station.

Turning to FIG. 27, the device 400 is shown with a charging dock 468 by which the device 400 may be charged. The charging dock 468 is a platform upon which the device 400 may be placed. The dock 468 may provide a flat surface, a recessed opening, or an inclined surface and have other variations commonly found in the art. Instead of a dock 468, a speaker charger or blue tooth speaker may be used to charge the device 400. Also, a wireless charging station may be used, such as a flat surface that the device 400 lays on and that allows the device 400 to charge wirelessly.

Figure 28:
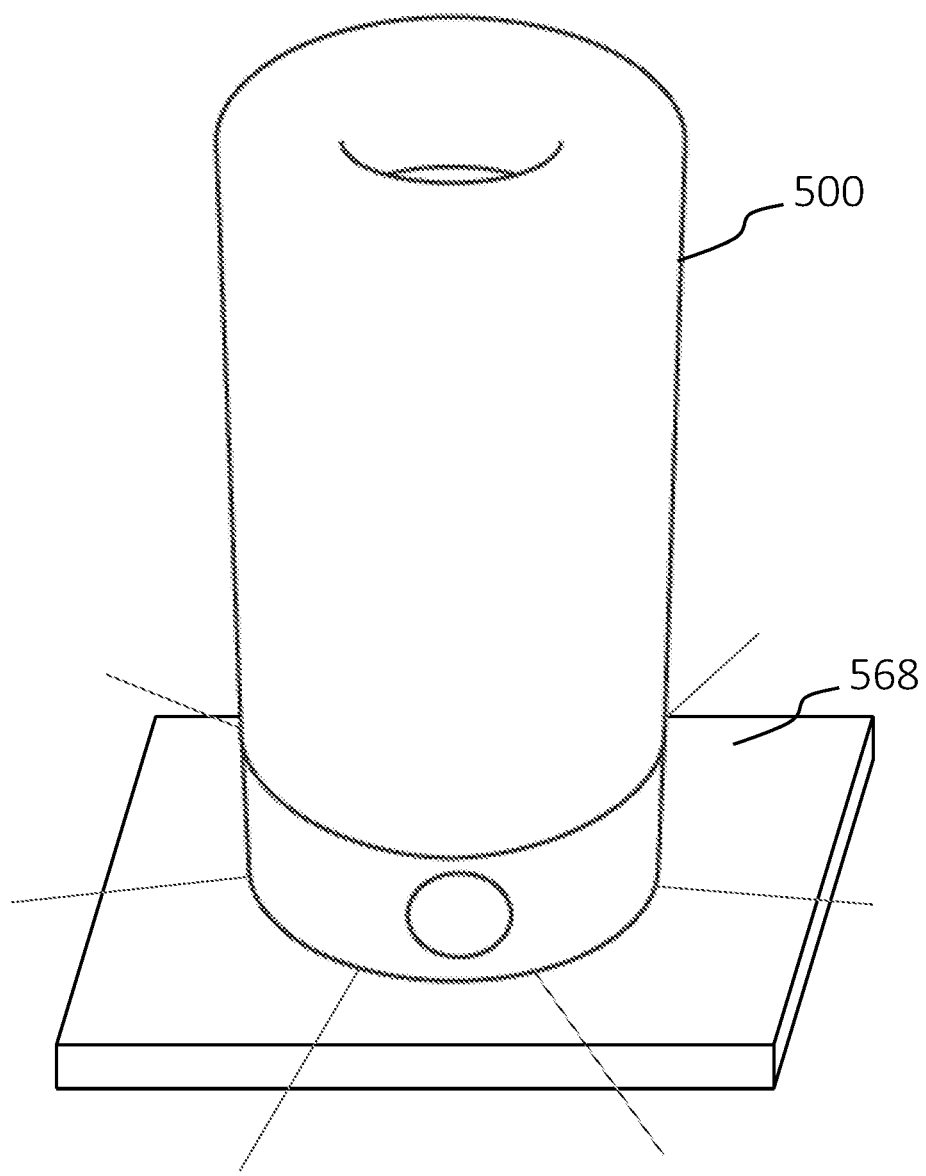
FIG. 28 illustrates a scent dispersion device including a docking station with lights.

The dock 568 may include a light-up feature with lights that light up as illustrated in FIG. 28. The dock 568 may light up when the device is connected to the dock or when the device is being charged by the dock 568. The dock 568 may light up depending on the type of fragrance in the cartridge. For example, each fragrance may be linked to a particular color, such that a certain shade of light lights up when an associated fragrance is being used in the device. Examples of associated lighting include purple lights to indicate lavender fragrance, light blue lights for linen fragrance, green lights for apple fragrance, and yellow lights for lemon grass fragrance. Not only does the light indicate the fragrance, but it psychologically reinforces or otherwise enhances the scent.

The dock 568 may also light up depending on the time of day. For a particular time of day, the dock may light up with a certain brightness, such as a bright light when it is daytime and a dim light when it is nighttime. The lighting is bright enough so that users can see it even during the daytime.

Besides a particular color, hue, or brightness, other types of lighting features, such as twinkling lights, blinking/solid, or lights shining in succession for a moving light effect, and other types of lighting may be used to indicate features of the device and communicate to the user.

Figure 29:
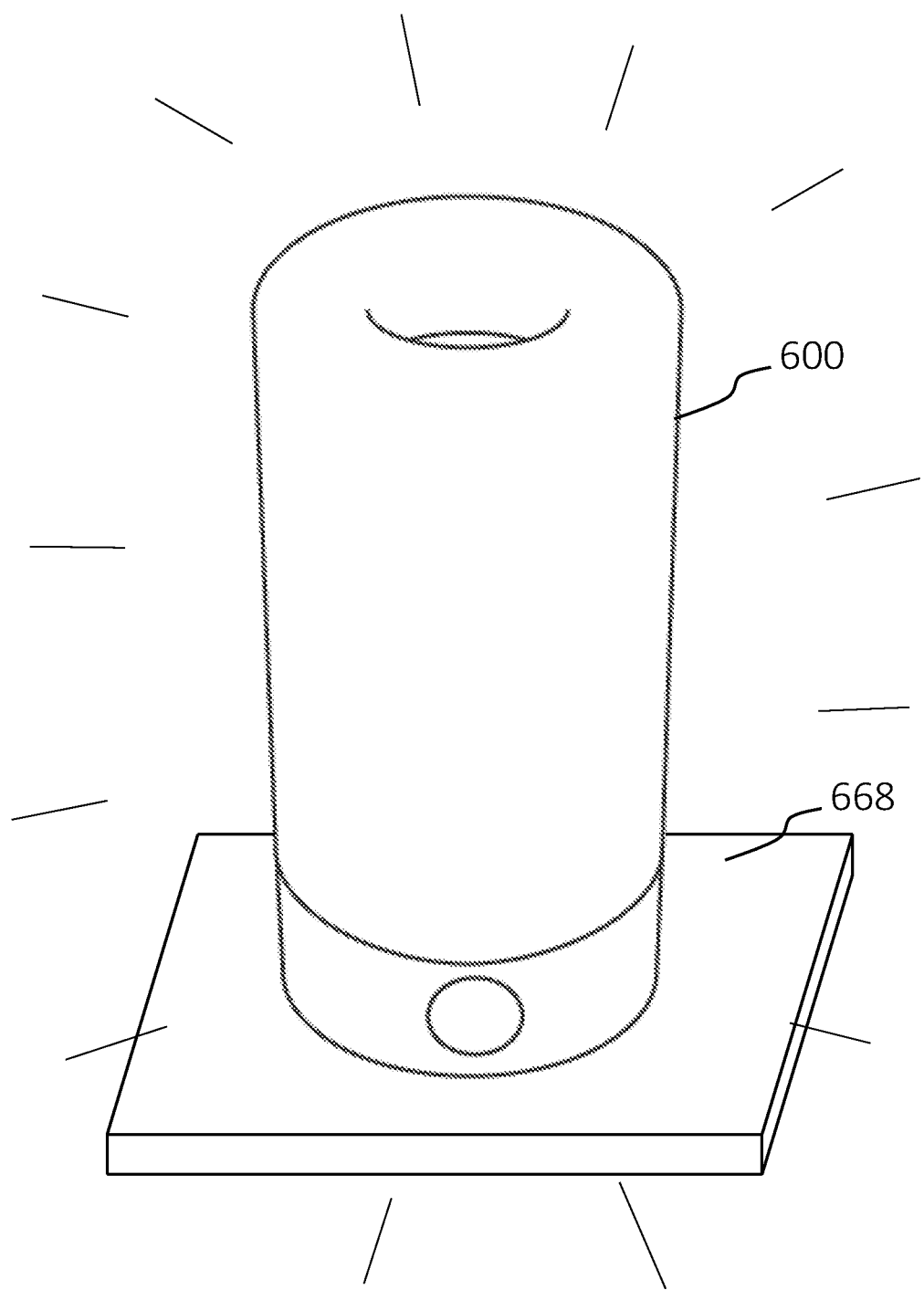
FIG. 29 illustrates a perspective view of a scent dispersion device with lights.

The device may include one or more lights that light up when the device is being used. FIG. 29 shows an example where the whole device 600 lights up. The dock 668 may or may not light up along with the device 600.

Figure 30:
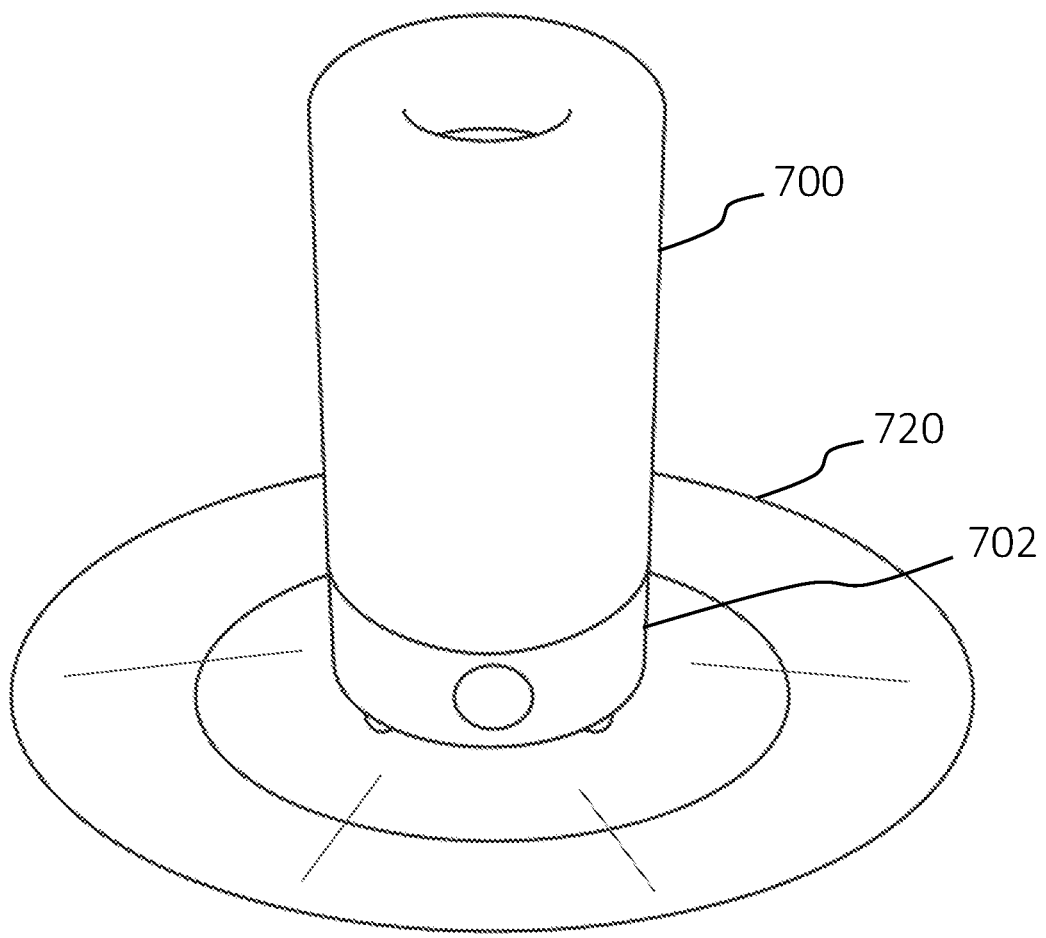
FIG. 30 illustrates a perspective view of a scent dispersion device with lights.

FIG. 30 shows the device 700 giving light from underneath the base 702. Lights from underneath the base 602 may light up in an evenly distributed manner around the device 700. Variations include that the dock also provide lighting that is evenly distributed in the same manner.

Figure 31A:
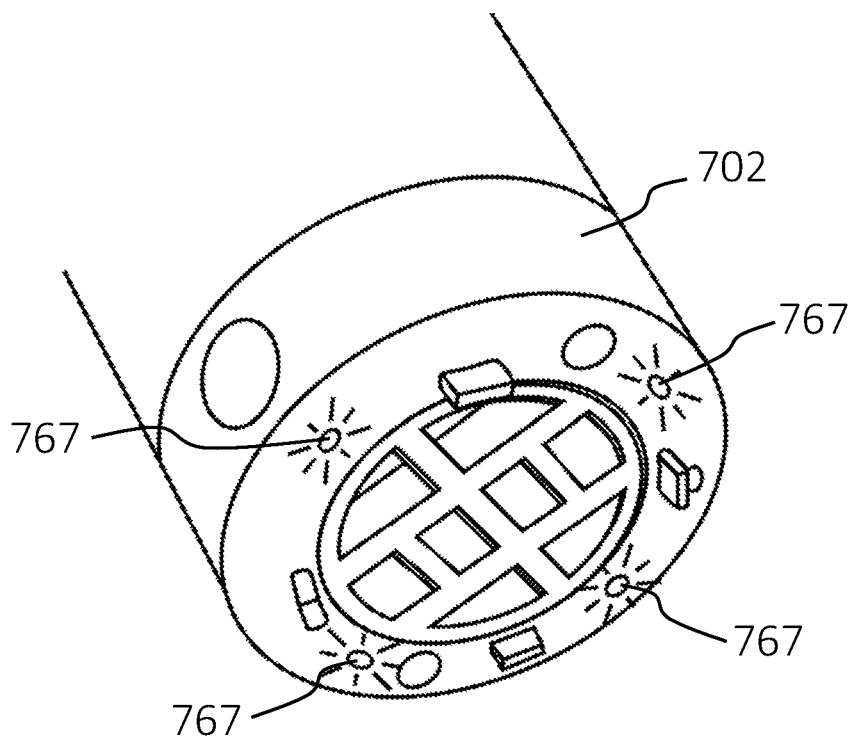
FIG. 31a illustrates a perspective view of a scent dispersion device with lights.
Figure 31B:
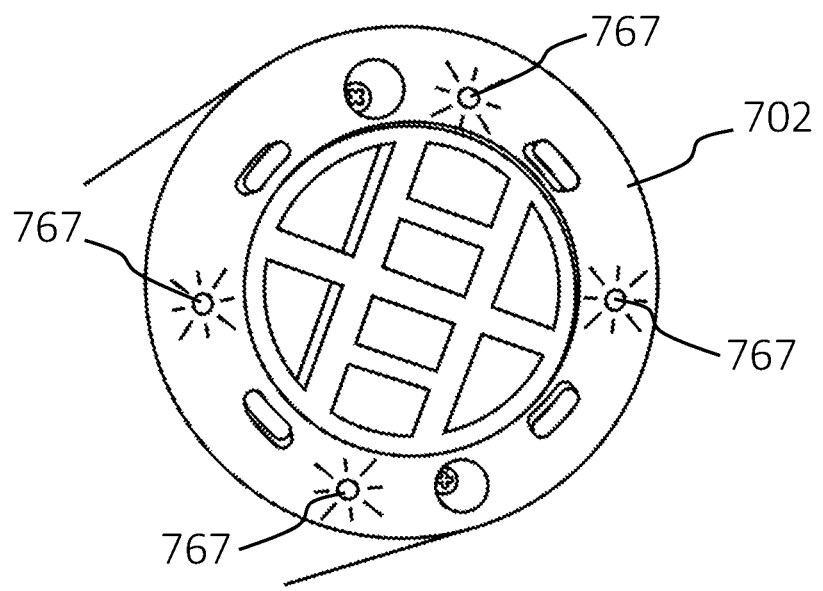
FIG. 31b illustrates a perspective view of a scent dispersion device with lights.

The lights may be LED lights, or other lights, that are located on the bottom panel of the device. Exemplary lights 767 are shown at opposite ends around edges on base 702 in FIGS. 31a and 31b.

Figures 32A, 32B:
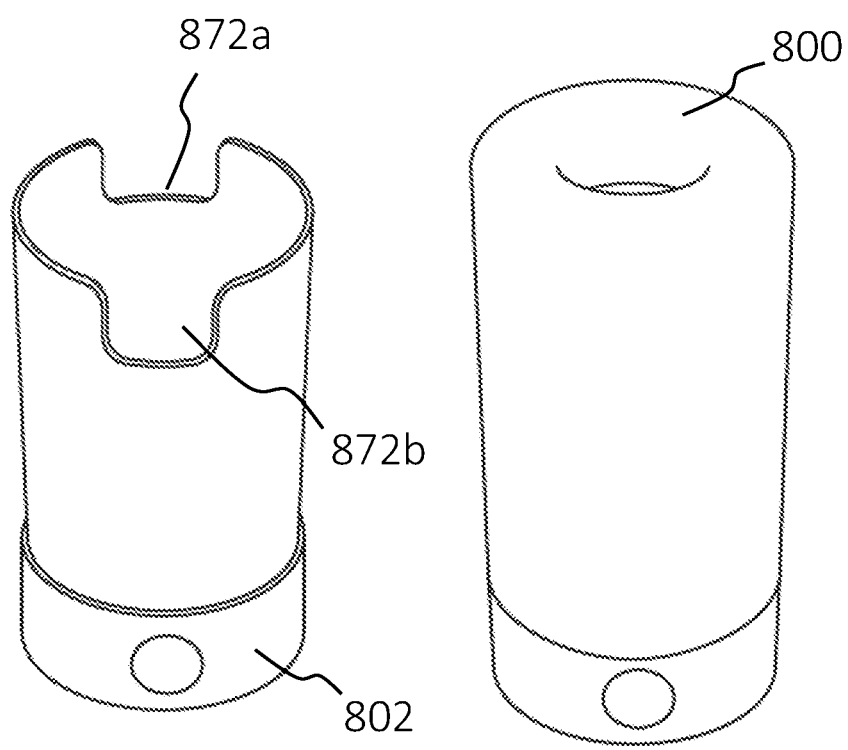
FIG. 32a illustrates a perspective view of a base with notches.
FIG. 32b illustrates a perspective view of a scent dispersion device.

FIGS. 32a and 32b illustrate a device 800 that includes a base 802 with notches 872a and 872b to allow the user to easily grasp the cartridge on opposite sides to remove a cartridge from the base. The notches 872a and 872b are defined by cutouts along the top edges of the base 802, the notches 872a and 872b being diametrically opposed from each other. The notches 872a and 872b have a depth that extend far enough into the base walls to provide gaps in the base that allow a user to use fingers to grasp part of the cartridge walls. The notches may extend to the base of the cartridge or farther. For example, the notches may extend to a filter located below the cartridge. Because the walls of the cartridge are solid, air does not readily escape through the notches 872a and 872b.

Figure 33:
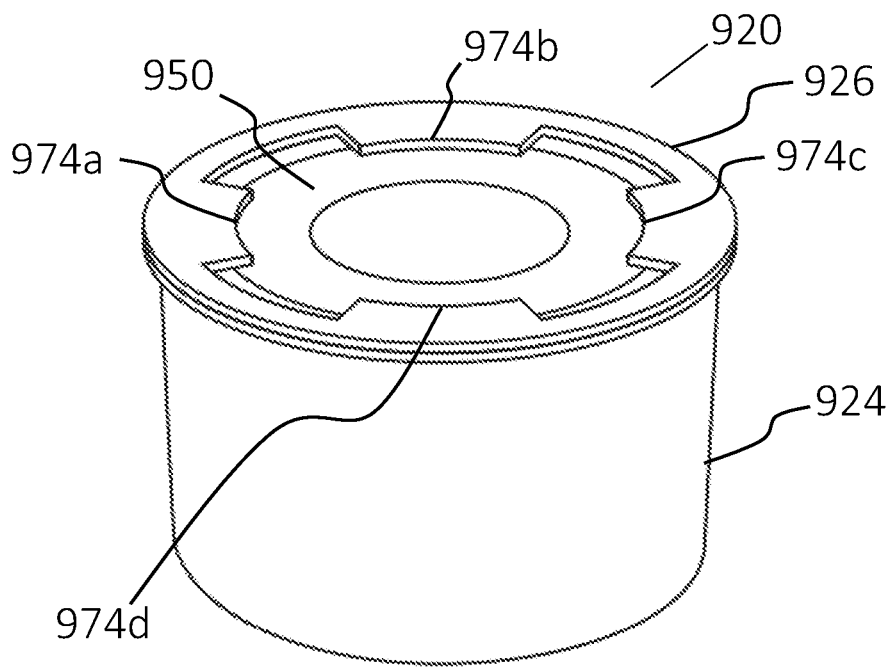
FIG. 33 illustrates a cartridge with locking tabs.
Figure 34:
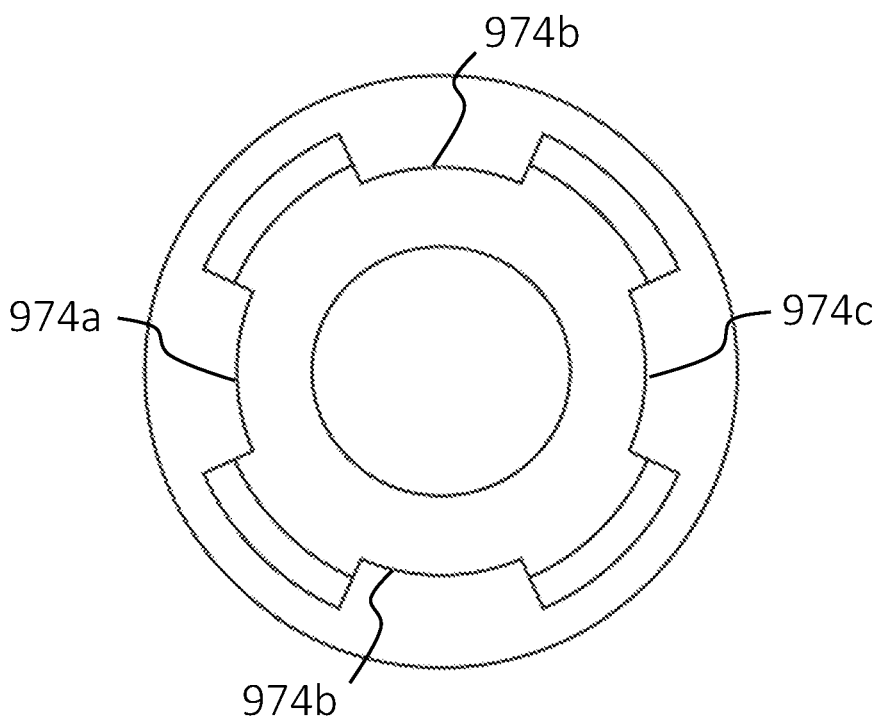
FIG. 34 illustrates a cartridge with locking tabs.

It may be desirable to keep the wick more securely held within the cartridge. FIGS. 33 and 34 illustrate locking tabs 974a, 974b, 974c, and 974d that hold the wick 950 inside the cup support 924 as an alternative construction for the cartridge 920. The tabs 974a, 974b, 974c, and 974d are elements that extend radially inward from the annular lip 926. They overlap edges of the wick 950 to hold it in place and make it difficult to remove from the cup support 924. They are of a flexible material which allow a user to still remove the wick 950 if necessary. For example, they may be made of the same material as the cup support, being molded as a natural extension of the annular lip.

Figure 35:
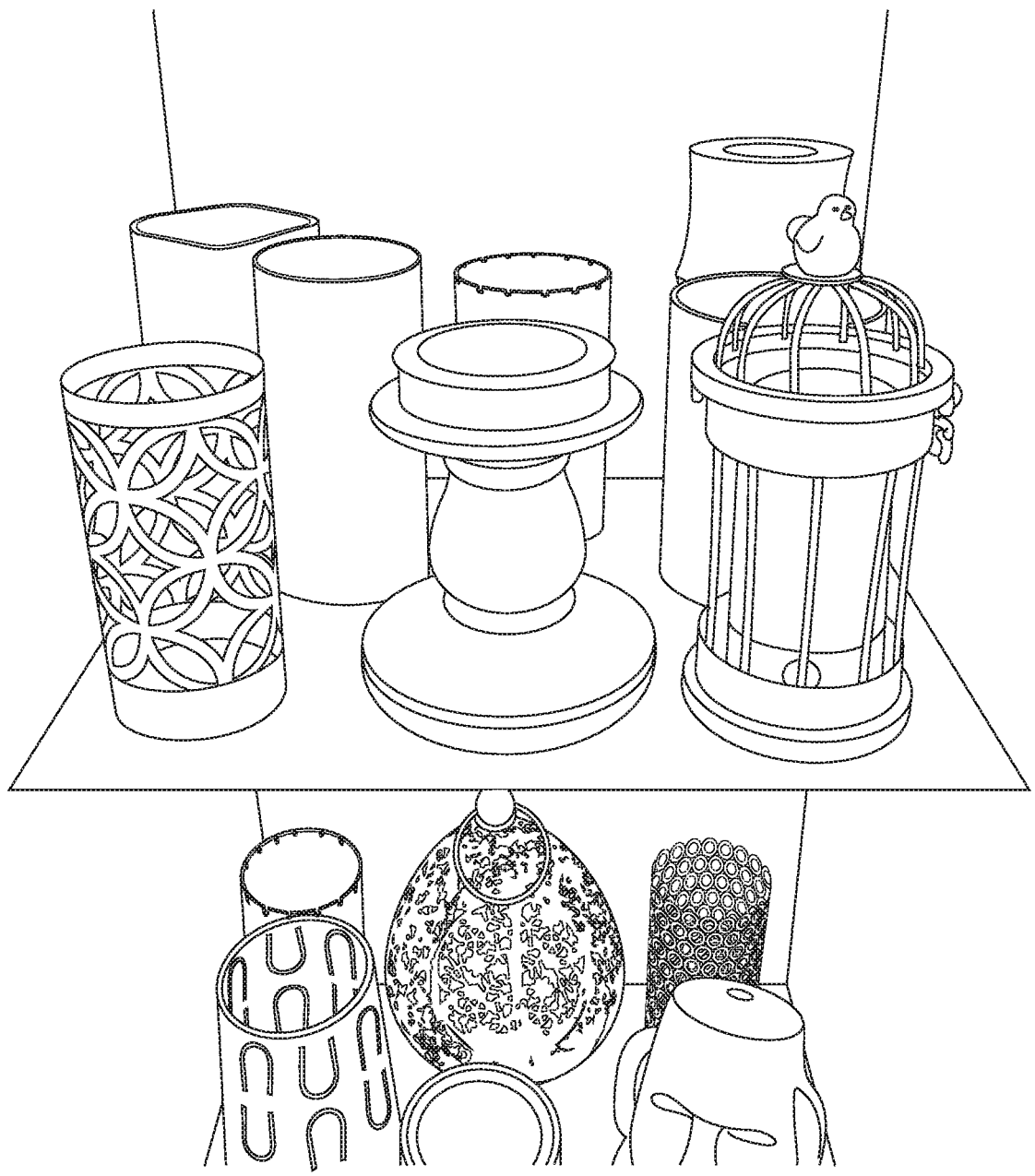
FIG. 35 illustrates a variety of decorative shells.
Figure 36:
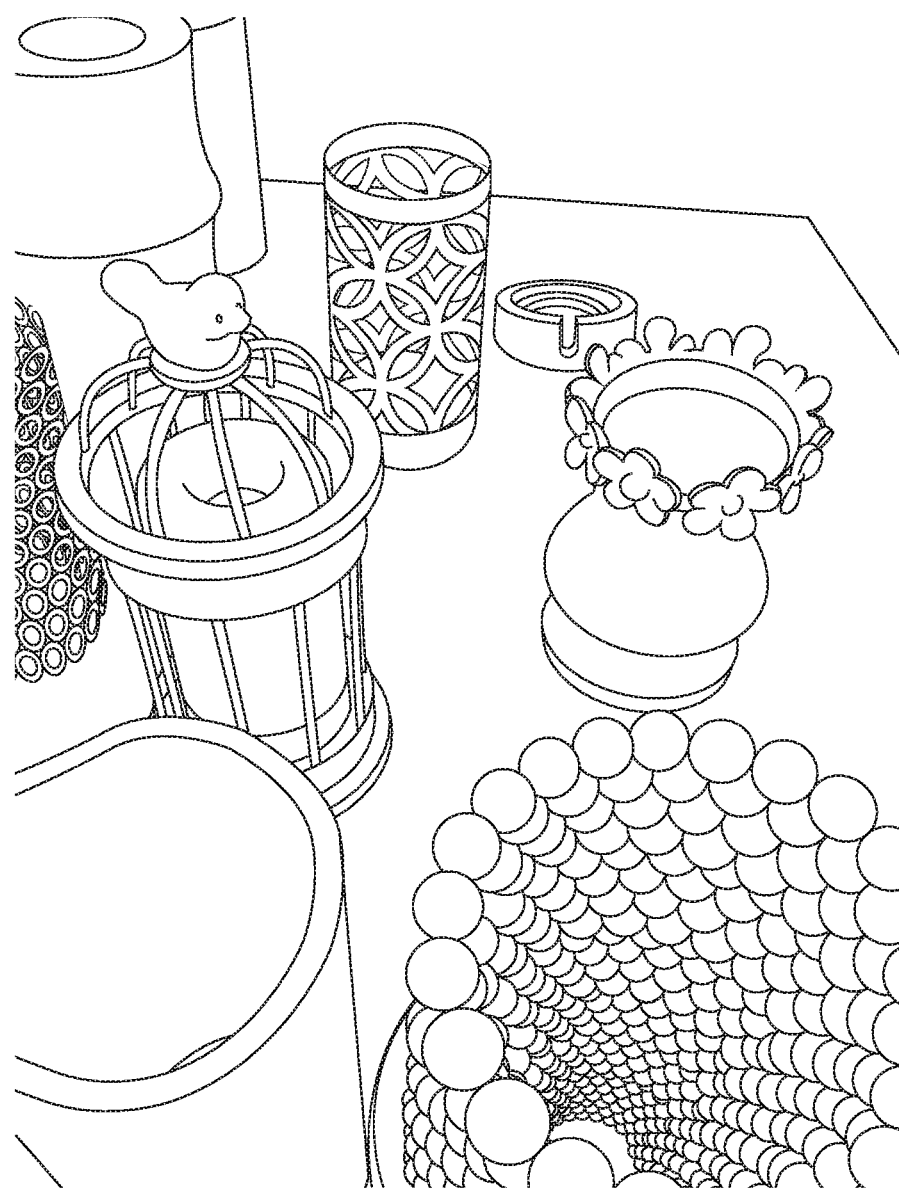
FIG. 36 illustrates a variety of decorative shells.

The cover may be plain or include one or more decorative elements. Alternatively, to provide additional aesthetic appeal and to comport with the décor of different rooms and color schemes, a variety of decorative shells that surround the device may be used. The shells may fit over the device, or contain the device within a shell housing. In some cases, the shells allow the device to be visible or partially visible. In other cases, the shells substantially obscure or completely hide the device. The shells may be of different sizes and shapes to add additional appeal and enable creative décor. The shell may be plain or may include several decorative elements, such as a sculpture, candle holder, model, etc. Examples of shells are shown in FIGS. 35 and 36.

Figure 37:
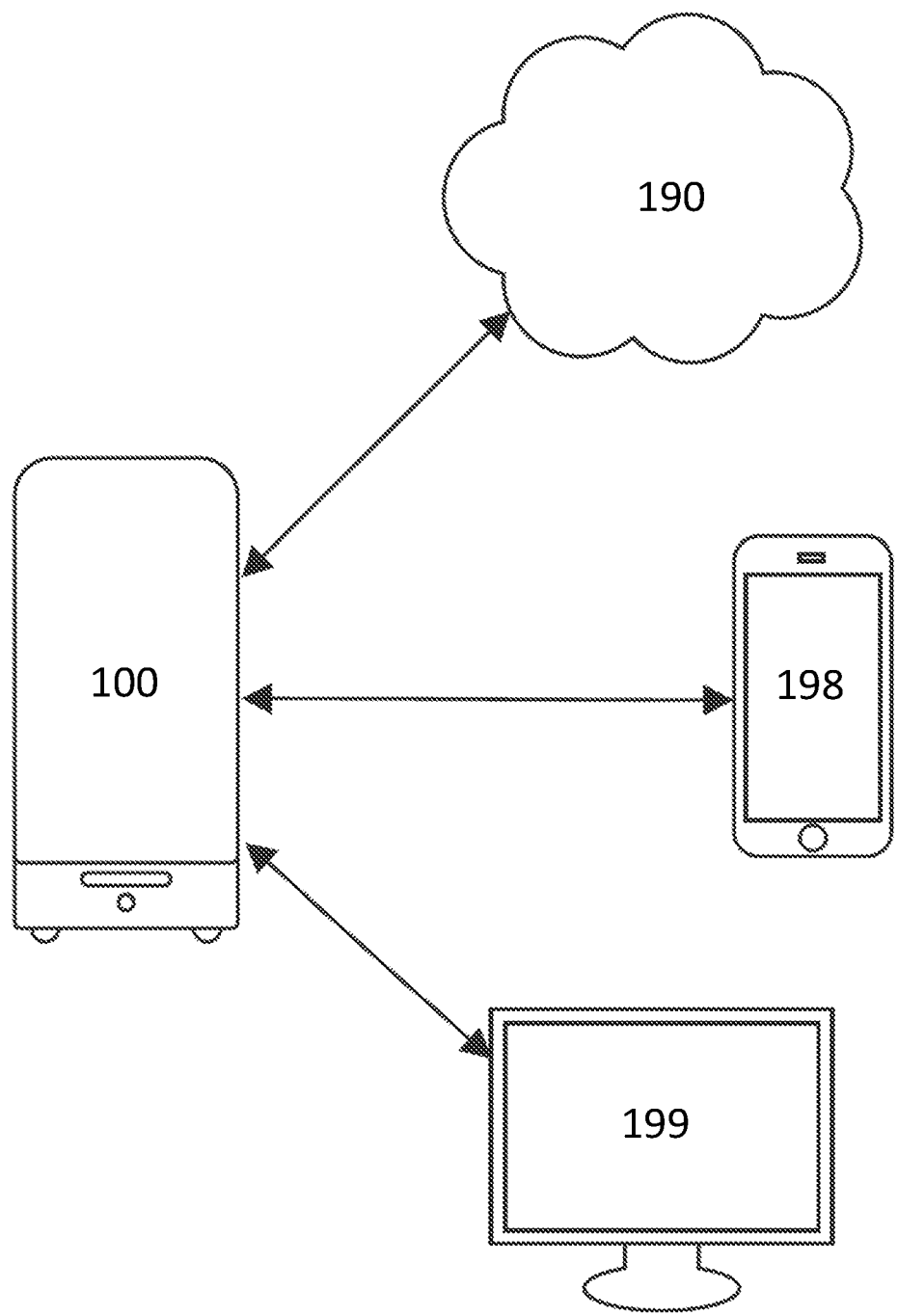
FIG. 37 illustrates a diagram of computer components used to implement features presented herein.

Turning to FIG. 37, a device 100 is shown connected to a network 190 (internet, network, or the cloud), an electronic device 198 (e.g. smart phone, personal display assistant), and a computer 199 (desktop computer, laptop, personal display assistant, virtual environment, or other known computing environment or technology). In this manner, the device 100 and its various features may be controlled and communicate with the controller of the device 100 to program and reset features.

The device 100 may further be in communication with an external source via any communication technology known in the art, including, but not limited to, direct wired communications, wired networks, direct wireless communications, wireless networks, local area networks, campus area networks, wide area networks, secured networks, unsecured networks, the Internet, any other computer communication technology known in the art, or any combination of such networks or communication technologies. Internet platforms may include Echo, Apple Homekit, and Google platform, for example. In a preferred embodiment, the device 100 is controlled by an application, or app.

Features that may be controlled include, for example, the timing of the device, the lighting of the device, fan speed, charge status, and button sequences to use and/or program the device. Timing of the device may include the length of time that the device is on and/or off. The timing may further include the time in which the lights are activated. Lighting may further be controlled according to fragrance, brightness, time of day, and other types of control.

One or more buttons (e.g., manual input 110 in FIG. 1) on the device may be programmed so that the device may be manually controlled on the device itself. For example, a button sequence may include holding down the button for three seconds to turn the device off or reset sequences. Another button sequence may include pressing the button three times to activate a 60 minute on/60 minute off repeat cycle. The sequences may be changed remotely over the various external sources described above. The following sequences are exemplary:

Sequence 1—Device is on full time

Sequence 2—Device will alternate on for 60 minutes and off for 60 minutes

Sequence 3—Turns on Bluetooth. When Bluetooth is activated, the fan will stop spinning and the light will blink. A user can now manage the settings from a smart phone.

Other means of control include voice and noise command. For example, voice recognition may be included such that the device recognizes audible words "on" and "off" and "sequence 1," etc., and activates the associated action to perform.

Figure 38:
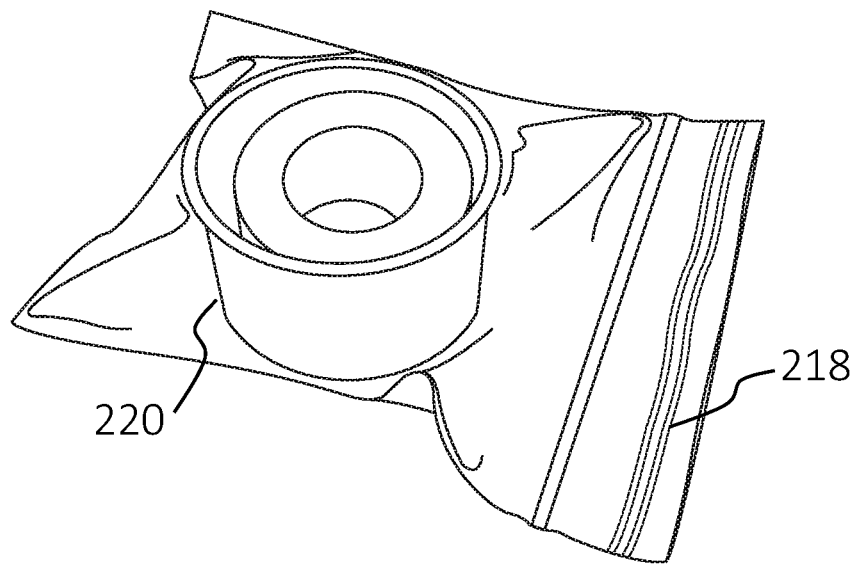
FIG. 38 illustrates a cartridge in a plastic bag.
Figure 39:
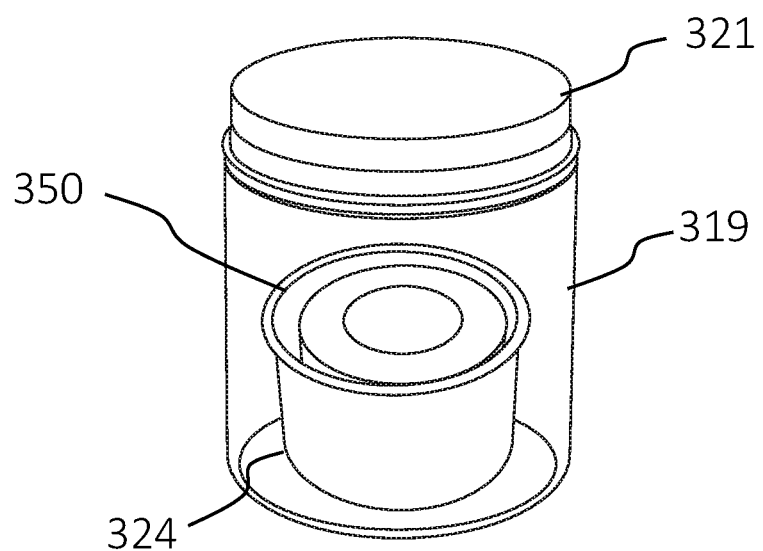
FIG. 39 illustrates a cartridge in a container.

As an alternative to top and bottom seals, the cartridge may be shipped and stored in conjunction with a container. As shown in FIG. 38, the cartridge 220 may be shipped, stored, and used in conjunction with a plastic bag 218. The plastic bag may have a removable seal, such as a sliding mechanism found in common plastic bags.

The device may further include that the wick or other type of porous material is configured to be used in a kit. The kit may include that the cartridge be put in a container with a removable lid, the removal of the lid providing an opening that allows scent to be naturally volatilized in the air. As shown in FIG. 27, an exemplary kit includes a cartridge 320 that is contained within a jar 319 (e.g., plastic, glass, etc.) that has a lid 319 (e.g., plastic, metal, etc.). Liquid fragrance may be poured into the jar 319, the wick absorbing the liquid fragrance therein. Although the wick 350 is shown with the cup support 320 so as to be a cartridge, embodiments include usage without a cup support. With a means of closure, such as a lid shown, the release of fragrance is controlled. Various other containers with and without lids are anticipated for use.

Note that the engagement of the cover and the base may vary. While the cover is described as being a single element, variations include that the cover include two parts that wrap around the base and join at ends. The two parts may be joined by a hinge that allow the two parts to open and close around the base.

Also, a slidable engagement to the base may be replaced by the cover fitting over the base and being engaged to the base by a locking mechanism. Other variations are also possible.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A scent dispersion device comprising:
   a housing;
   a fan and a controller within the housing, the fan controlled by the controller for directing air up through a top, central orifice of the housing, the housing streamlined to direct air flow up through the top, central orifice; and
   a refill cartridge within the housing having a porous body retaining a volatile substance, the refill cartridge located in air flow directed by the fan and constructed such that air flow directed from the fan flows through the refill cartridge and out of the top, central orifice of the housing having a vertical path to volatilize the volatile substance into air.

2. The device of claim 1, wherein the refill cartridge is located above the fan.

3. The device of claim 1, wherein the housing comprises a base and a cover engaged with the base.

4. The device of claim 2, wherein a base holds the refill cartridge and the housing further comprises a cover over at least a portion of the base, the cover including top, central orifice for air to flow out of the housing.

5. The device of claim 2, further comprising an air filter within the housing, the air filter positioned in directed air by the fan before it flows through the refill cartridge, the air filter configured to scrub the air before the air flows through the refill cartridge.

6. The device of claim 3, further comprising an insert ring that fits underneath the cover, the insert ring configured to direct and provide a streamlined air flow out of the top of the orifice.

7. The device of claim 1, wherein the controller is configured to be powered by a battery within the housing.

8. The device of claim 1, further comprising remote access and control of the device provided by a computer-implemented remote control system and a user interface.

9. The device of claim 1, wherein the refill cartridge comprises a cup support containing the porous body, the cup support having openings at each end for passage of air.

10. The device of claim 9, wherein the openings of the cup support are sealable by removable foil or film.

11. The device of claim 9, wherein the porous body has one or more holes therethrough that align with openings of the cup support to thus provide one or more air paths through the porous body and the cup support.

12. The device of claim 1, wherein inner walls of the housing define a streamlined air flow between the refill cartridge and the orifice.

13. The device of claim 3, wherein the base includes one or more air inlets such that air is directed through the air inlets, and up through the housing.

14. The device of claim 1, wherein the housing includes air inlets on sidewalls such that air is directed from outside the housing and through the air inlets and up through the housing.

15. The device of claim 2, further comprising a decorative shell that includes decorative elements, the shell at least partially covering the device.

16. The device of claim 3, wherein an exterior surface of the cover includes decorative elements.

17. A scent dispersion device comprising:
    a housing;
    a fan and a controller within the housing, the fan controlled by the controller for directing air up through the housing;
    a refill cartridge within the housing having a porous body retaining a volatile substance, the refill cartridge located in air flow directed by the fan and constructed such that air flow directed from the fan flows through the refill cartridge and out of the housing to volatilize the volatile substance into air, the refill cartridge having a constricting air flow construction to streamline air flow into the refill cartridge.

18. A refill cartridge for a scent dispersion device comprising:
    a cup support containing a wick, the cup support having a stream constrictor that is funnel shaped with curved walls defining a first opening at a bottom of the cup support and then curving inward toward a top of the cup support to direct and streamline vertical air flow toward the top of the cup support.

19. A scent dispersion device comprising:
    a housing;
    a fan and a controller within the housing, the fan controlled by the controller for directing air up through the housing;
    a refill cartridge within the housing, the refill cartridge comprising a body that retains a volatile substance, the refill cartridge and the body constructed with a central opening and positioned in air directed from the fan such that air flows to volatilize the volatile substance in the air by being directed from at least one bottom opening of the housing located below the fan and a bottom of the refill cartridge to a top of the refill cartridge with the air exiting out the top of the refill cartridge and through a top orifice of the housing,
    the housing, the fan, the cartridge, and the body in axial alignment such that the air flow has a vertical pathway unobstructed as it flows from the at least one bottom opening through the central opening and out of the top orifice.

20. The device of claim 19, wherein the housing is streamlined to direct air flow out through the top orifice of the housing.

* * * * *